United States Patent
Oefner

(12)
(10) Patent No.: US 6,453,244 B1
(45) Date of Patent: *Sep. 17, 2002

(54) DETECTION OF POLYMORPHISMS BY DENATURING HIGH-PERFORMANCE LIQUID CHROMATOGRAPHY

(75) Inventor: Peter J. Oefner, Redwood City, CA (US)

(73) Assignee: Stanford University, Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/502,558

(22) Filed: Feb. 10, 2000

(51) Int. Cl.[7] .................... G01N 33/483; G01N 30/04; G01N 30/30; C07H 21/00
(52) U.S. Cl. ................ 702/20; 435/6; 536/24.3; 536/25.4; 536/25.5
(58) Field of Search .................... 435/6, 91.2, 91.1; 536/24.3, 24.31–24.33, 25.4, 25.42, 25.5; 73/61.53, 61.55; 210/661; 702/20

(56) References Cited

U.S. PATENT DOCUMENTS 5,795,976 A * 8/1998 Oefner .................. 536/25.4
5,935,781 A * 8/1999 Poirier .................. 435/6

OTHER PUBLICATIONS

O'Donovan et al. Blind analysis of denaturing high–performance liquid chromatography as a tool for mutation detection. Genomics, vol, 52, pp. 44–49 (1998).*
Liu et al. Denaturing high performance liquid chromatography (DHPLC) used in the detection of germline and somatic mutations. Nucleic Acids Research, vol. 26(6), pp. 1396–1400 (1998).*
Cargill et al, Nature Genet. 22 (1999) 231–238.
Chee et al., Science 274 (1996) 610–614.
Chen et al., Genome Res. 9 (1999) 492–498.
Cho et al., Nature Genet. 23 (1999) 203–207.
Collins et al., Science 278 (1997) 1580–1581.
Germer and R. Higuchi, Genome Res. 9 (1999) 72–78.
Giordano et al., Genomics, 56 (1999) 247–253.
Haff and Smirnov, Genome Res. 7 (1997) 378–388.
Hayward–Lester et al., in: F. Ferr(–) (Ed.), Gene Quantification, Birkhäusr Verlag, 1997, pp. 44–77.
Higgins et al., BioTechniques 23 (1997) 710–714.
Hoogendoorn et al., Hum. Genet. 104 (1999) 89–93.
Huber et al., Anal. Biochem. 212 (1993) 351–358.
Jalanko et al., Clin. Chem. 38 (1992) 39–43.
Kwok et al., Genomics 31 (1996) 123–126.
Kruglyak, Nature Genet. 17 (1997) 21–24.
Lee et al., Nucl. Acids Res. 21 (1993) 3761–3766.
Livak et al., PCR Methods Appl. 4 (1995) 357–362.
Newton et al, Nucl. Acids Res. 17 (1989) 2503–2516.
Nickerson et al., Proc. Natl. Acad. Sci. USA 87 (1990) 8923–8927.
Nikiforov et al., Nucl. Acids Res. 22 (1994) 4167–4175.
Nyren et al, Anal. Biochem. 208 (1993) 171–175.
Pastinen et al., Clin. Chem. 42 (1996) 1391–1397.
Piggee et al., J. Chromatogr. A 781 (1997) 367–75.
Risch and Merikangas, Science 273 (1996) 1516–1517.
Saiki et al., Science 230 (1985), 1350–1354.
Saiki et al., N. Engl. J. Med. 319 (1988) 537–541.
Underhill et al., Genome Res. 7 (1997) 996–1005.
Underhill et al., Genome Res. 7 (1997) 996–1005.
Wang et al., Science 280 (1998) 1077–1082.
Winzeler et al., Science 281 (1998) 1194–1197.
Wu et al. Proc. Natl. Acad. Sci. USA 86 (1989) 2757–2760.
Wu and Wallace, Genomics 4 (1989) 560–560.

* cited by examiner

Primary Examiner—John S. Brusca
Assistant Examiner—Marjorie A Moran
(74) Attorney, Agent, or Firm—Bozicevic, Field & Francis LLP; Carol L. Francis

(57) ABSTRACT

The present invention provides a method for detecting polymorphisms in a nucleic acid by preconditioning a sample of nucleic acids to completely denature the nucleic acids, e.g., via heating and/or chemical treatment, and performing high-performance liquid chromatography (HPLC) on the nucleic acid under denaturing conditions to identify any polymorphisms. The nucleic acids to be analyzed are completely denatured prior to application of the sample to a stationary reverse-phase support and throughout the HPLC process. Sample elution is also carried out under completely denaturing conditions, and the sample mixture is eluted with a mobile phase containing an ion-pairing reagent and an organic solvent.

30 Claims, 10 Drawing Sheets

SEQUENCE LISTING

<160> NUMBER OF SEQ ID NOS: 40

<210> SEQ ID NO 1
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 1
tccatgaatc actccc                                                         16

<210> SEQ ID NO 2
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 2
tccatgaatc actccg                                                         16

<210> SEQ ID NO 3
<211> LENGTH: 16
<212> TYPE: DNA
<213> ORGANISM: Artificial Sequence
<220> FEATURE:

```
<223> OTHER INFORMATION: synthetic oligonucleotide

<400> SEQUENCE: 3
tccatgaatc actcca                                                            16

<210> SEQ ID NO 4
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 4
tccatgaatc actcct                                                            16

<210> SEQ ID NO 5
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 5
gtgctcagtg tggcccagga tc                                                     22

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 6
gtgctcagtg tcgcccagga tc                                                     22

<210> SEQ ID NO 7
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 7
gtgctcagtg tagcccagga tc                                                     22

<210> SEQ ID NO 8
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 8
gtgctcagtg ttgcccagga tc                                                     22

<210> SEQ ID NO 9
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 9
aaaccacatt ctgagcatac cccccaaaaa tttcatgccg aagctgtggt c                     51
```

```
<210> SEQ ID NO 10
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 10
aaaccacatt ctgagcatac ccccaaaaaa tttcatgccg aagctgtggt c           51

<210> SEQ ID NO 11
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 11
caacttaatc agatttagga cacaaaagca actacataat gaaaagaga gctggtga      58

<210> SEQ ID NO 12
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 12
caacttaatc agatttagga cacaaaagct actacataat gaaaagaga gctggtga      58

<210> SEQ ID NO 13
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 13
gaaacggcct aagatggttg aatgctcttt attttctttt aatttagaca tgttcaaa     58

<210> SEQ ID NO 14
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 14
gaaacggcct aagatggttg aatcctcttt attttctttt aatttagaca tgttcaaa     58

<210> SEQ ID NO 15
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 15
gactttttgt acccaccatt tgtggaacta aattatatca gtacaaaaag ggctacattc   60

<210> SEQ ID NO 16
<211> LENGTH: 60
<212> TYPE: DNA
<213> ORGANISM: Artificial Sequence
<220> FEATURE:
<223> OTHER INFORMATION: synthetic oligonucleotide
```

```
<400> SEQUENCE: 16 gacttttgt acccaccatt tgtggaacta aattgtatca gtacaaaaag ggctacattc      60

<210> SEQ ID NO 17
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 17
agacagttct tcaggaaaac acctcctttg gactcacacc atgtgttttc cattcaaatt    60
a                                                                    61

<210> SEQ ID NO 18
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 18
agacagttct tcaggaaaac accttctttg gactcacacc atgtgttttc cattcaaatt    60
a                                                                    61

<210> SEQ ID NO 19
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 19
cccaaaccca ttttgatgct tgacttaaaa ggtcttcaat tattattttc ttaaatattt    60
tg                                                                   62

<210> SEQ ID NO 20
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 20
cccaaaccca ttttgatgct ttacttaaaa ggtcttcaat tattattttc ttaaatattt    60
tg                                                                   62

<210> SEQ ID NO 21
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 21
ccattgagga acaacataca gcttctgttc ggcctcggct gtgggctc                 48

<210> SEQ ID NO 22
<211> LENGTH: 48
<212> TYPE: DNA
<213> ORGANISM: Artificial Sequence
<220> FEATURE:
<223> OTHER INFORMATION: synthetic oligonucleotide
```

<400> SEQUENCE: 22
ccattgagga acaacataca gcttctgttc gacctcggct gtgggctc          48

<210> SEQ ID NO 23
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 23
aataaacctt tacggggcta agcctcagac ctgcaagctg cttgttatag          50

<210> SEQ ID NO 24
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 24
aataaacctt tacggggcta agccttagac ctgcaagctg cttgttatag          50

<210> SEQ ID NO 25
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 25
agacatctga ctcccagcat gaacggtccc aactcctctc taacaaaagg taa       53

<210> SEQ ID NO 26
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 26
agacatctga ctcccagcat gaatggtccc aactcctctc taacaaaagg taa       53

<210> SEQ ID NO 27
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 27
tttgttcata cggtcaatat tcgatactct cagtcctcac tgctggtcct tacg      54

<210> SEQ ID NO 28
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 28
tttgttcata cggtcaatat tcgattctct cagtcctcac tgctggtcct tacg      54

<210> SEQ ID NO 29

```
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 29
cgaaaaagaa gatggtgagt tcacttttta cctcaataaa acccttaca taaa            54

<210> SEQ ID NO 30
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 30
cgaaaaagaa gatggtgagt tcactttca cctcaataaa accctttaca taaa             54

<210> SEQ ID NO 31
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 31
gctccatttg aaggttctat aactgaaact agaataccta agctatgggg aactaaactc      60
tgaat                                                                 65

<210> SEQ ID NO 32
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 32
gctccatttg aaggttctat aactgaaact agaatacata agctatgggg aactaaactc      60
tgaat                                                                 65

<210> SEQ ID NO 33
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 33
gataagccat atgatccagc aggattaatt cctttaccg tttaattagt cgtagatact       60
caagacagac cgt                                                        73

<210> SEQ ID NO 34
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 34
gataagccat atgatccagc aggattaatt cctttactg tttaattagt cgtagatact       60
caagacagac cgt                                                        73
```

```
<210> SEQ ID NO 35
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 35
tgtcctttag tttctatttg gttttatata ttatcatatg aactataaag aaggttgaag     60
caaagaacag ccaaataat                                                  79

<210> SEQ ID NO 36
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 36
tgtcctttag tttctatttg gttttatata ttatcatatg aactataaag aagattgaag     60
caaagaacag ccaaataat                                                  79

<210> SEQ ID NO 37
<211> LENGTH: 94
<212> TYPE: DNA
<213> ORGANISM: Artificial Sequence
<220> FEATURE:
<223> OTHER INFORMATION: synthetic oligonucleotide

<400> SEQUENCE: 37
tggagtattt ctctagcttg ctgaaataat gccaaatttt ataatatgat actagcaaca     60
caaatattta gctaaaatta cgttgcatta aaaa                                 94

<210> SEQ ID NO 38
<211> LENGTH: 94
<212> TYPE: DNA
<213> ORGANISM: Artificial Sequence
<220> FEATURE:
<223> OTHER INFORMATION: synthetic oligonucleotide

<400> SEQUENCE: 38
tggagtattt ctctagcttg ctgaaataat ggcaaatttt ataatatgat actagcaaca     60
caaatattta gctaaaatta cgttgcatta aaaa                                 94

<210> SEQ ID NO 39
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 39
tgtaaaacga cggccagt                                                   18

<210> SEQ ID NO 40
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 40
caggaaacag ctatgacc                                                   18
```

DETECTION OF POLYMORPHISMS BY DENATURING HIGH-PERFORMANCE LIQUID CHROMATOGRAPHY

GOVERNMENT RIGHTS

The United States Government may have certain rights in this application pursuant to NIH grant HG01707.

FIELD OF THE INVENTION

The present invention relates to a chromatographic method for the detection or analysis of polymorphisms in nucleic acids, and particularly to denaturing high performance liquid chromatography for such uses.

BACKGROUND OF THE INVENTION

Approximately 4,000 human disorders are attributed to heritable genetic causes. Hundreds of genes responsible for various disorders have been mapped, and sequence information is being accumulated rapidly. A principal goal of the Human Genome Project is to find all genes associated with each disorder.

The most reliable diagnostic test for any specific genetic disease (or predisposition to a particular disease) is the identification of polymorphic variations in DNA sequence in affected cells that result in altered gene function and/or expression levels. In addition, certain polymorphic variations that are associated with predispositions for disorders, e.g., alleles that are associated with disease such as certain forms of cancer or Alzheimer's disease, may allow prophylactic measure to be taken to help reduce or reverse the risk imposed by the polymorphic allele. Furthermore, responses to specific medications may depend on the presence of polymorphisms, making people with a particular polymorphism a better candidate for a medication than those not possessing the polymorphism. These and other reasons provide a great impetus for developing DNA or RNA screening as a practical tool for medical diagnostics.

Genetic polymorphisms and mutations can manifest themselves in several forms, such as point polymorphisms or point mutations where a single base is changed to one of the three other bases, deletions where one or more bases are removed from a nucleic acid sequence and the bases flanking the deleted sequence are directly linked to each other, insertions where new bases are inserted at a particular point in a nucleic acid sequence adding additional length to the overall sequence, and expansions and reductions of repeating sequence motifs. Large insertions and deletions, often the result of chromosomal recombination and rearrangement events, can lead to partial or complete loss of a gene. Of these forms of polymorphism, in general point polymorphisms are the most difficult to detect because they represent the smallest degree of molecular change.

The most definitive screening method to identify and determine polymorphisms such as SNPs in a nucleic acid requires determining the actual base sequence (Maxam and Gilbert, 1977; Sanger et al., 1977). Although such a method is the most accurate, it is also the most expensive and time consuming method. Restriction mapping analysis has some limited use in analyzing DNA for polymorphisms. If one is looking for a known polymorphism at a site which will change the recognition site for a restriction enzyme, it is possible simply to digest DNA with this restriction enzyme and analyze the relative sizes and numbers of fragments to determine the presence or absence of the polymorphism. (R. K. Saiki et al., Science 230 (1985), 1350–1354). This type of analysis is also useful for determining the presence or absence of gross insertions or deletions, but may not be useful in detecting smaller changes that do not result in a readily distinguishable change in restriction fragment size and/or number. Restriction mapping methods also generally require the use of hybridization techniques which are time consuming and costly.

The large-scale identification of single-nucleotide polymorphisms (SNPs) in the human as well as other model genomes such as yeast and Arabidopsis thaliana has been accomplished by methods such as fluorescence-based sequencing (P.-Y. Kwok, Q. et al., Genomics 31 (1996) 123–126), hybridization high-density variation-detection DNA chips (D. G. Wang et al., Science 280 (1998) 1077–1082; E. A. Winzeler et al., Science 281 (1998) 1194–1197), and high performance liquid chromatography (P. A. Underhill et al., Genome Res. 7 (1997) 996–1005; M. Giordano et al., Genomics, 56 (1999) 247–253; R. J. Cho et al., Nature Genet. 23 (1999) 203–207; and M. Cargill et al, Nature Genet. 22 (1999) 231–238). These and other methods have been used to identify thousands of SNPs. For this reason, the development of simple and inexpensive technology for the genotyping of SNPs of individuals (e.g., in a clinical setting) has become of great interest as the ability to discriminate between allelic forms of SNPs is increasingly seen as fundamental to future molecular genetic analysis of disease (N. Risch and K. Merikangas, Science 273 (1996) 1516–1517; F. S. Collins et al., Science 278 (1997) 1580–1581; L. Kruglyak, Nature Genet. 17 (1997) 21–24).

A number of additional methods are available for SNP genotyping such as allele-specific hybridization (R. K. Saiki et al., N. Engl. J. Med. 319 (1988) 537–541; M. Chee et al., Science 274 (1996) 610–614), nick translation PCR (L. G. Lee et al., Nucl. Acids Res. 21 (1993) 3761–3766; K. J. Livaket al., PCR Methods Appl. 4 (1995) 357–362), ligase chain reaction (D. Y. Wu and R. B. Wallace, Genomics 4 (1989) 560–560; D. A. Nickerson et al., Proc. Natl. Acad. Sci. USA 87 (1990) 8923–8927), allele-specific polymerase chain reaction (C. R. Newton et al, Nucl. Acids Res. 17 (1989) 2503–2516; D. Y. Wu et al. Proc. Natl. Acad. Sci. USA 86 (1989) 2757–2760); $T_m$-shift genotyping (S. Germer and R. Higuchi, Genome Res. 9 (1999) 72–78), and minisequencing (A. Jalanko et al., Clin. Chem. 38 (1992) 39–43; P. Nyren et al., Anal. Biochem. 208 (1993) 171–175; T. T. Nikiforov et al., Nucl. Acids Res. 22 (1994) 4167–4175; T. Pastinen et al., Clin. Chem. 42 (1996) 1391–1397; G. S. Higgins et al., BioTechniques 23 (1997) 710–714; L. A. Haff and I. P Smirnov, Genome Res. 7 (1997) 378–388; C. A. Piggee et al., J. Chromatogr. A 781 (1997) 367–75; X. Chen et al., Genome Res. 9 (1999) 492–498; and B. Hoogendoom et al., Hum. Genet. 104 (1999) 89–93). The latter method, which is based on the annealing of a primer immediately upstream or downstream from the polymorphic site and its extension by one or more bases in the presence of the appropriate dNTPs and ddNTPs, has become very popular. It has been combined with a variety of techniques for detecting the extension products, including radiolabeling (A. Jalanko et al., Clin. Chem. 38 (1992) 39–43), luminous detection (P. Nyren et al, Anal. Biochem. 208 (1993) 171–175), colorimetric ELISA (T. T. Nikiforov et al., Nucl. Acids Res. 22 (1994) 4167–4175), gel-based fluorescent detection (T. Pastinen et al., Clin. Chem. 42 (1996) 1391–1397), mass spectrometry (G. S. Higgins et al., BioTechniques 23 (1997) 710–714; L. A. Haff and I. P Smirnov, Genome Res. 7 (1997) 378–388), capillary electrophoresis (C. A. Piggee et al., J. Chromatogr. A 781 (1997) 367–75), fluorescence polarization (X. Chen et al., Genome Res. 9

(1999) 492–498), and most recently high-performance liquid chromatography (B. Hoogendoom et al., Hum. Genet. 104 (1999) 89–93).

All of the aforementioned genotyping techniques use the polymerase chain reaction as the initial sample pretreatment step. Many of these techniques thus require at least a two-step process to determine the presence of an SNP. Although some of the methods can be done in a single step in a single tube, these techniques require expensive fluorescent dye-labeled oligonucleotide probes (L. G. Lee et al., Nucl. Acids Res. 21 (1993) 3761–3766.; K. J. Livak et al., PCR Methods Appl. 4 (1995) 357–362). Others require additional steps such as hybridization or primer extension. Primer extension also requires prior purification of the PCR product from unincorporated dNTPs and oligonucleotides by either solid-phase extraction or enzymatic treatment with Shrimp Alkaline Phosphatase and Exonuclease I. For these reasons, genotyping is still a far more costly undertaking than identifying the presence of an SNP in the genome. This constitutes a severe limitation in the application of SNPs to genetic studies in the clinic and laboratories.

High-performance liquid chromatography (HPLC) has been used to identify and analyze polymorphisms in DNA, for example by detecting the presence of heteroduplices in DNA samples from an individual. The importance of pre-conditioning DNA prior to its contact with the column matrix had been recognized for the successful resolution of homo- and heteroduplex species under partially denaturing conditions, as it proved impossible to detect heteroduplices when the DNA sample was injected directly into the column without such preconditioning. (A. Hayward-Lester et al., in: F. Ferré (Ed.), *Gene Quantification*, Birkhäuser Verlag, 1997, pp. 44–77; U.S. Pat. No. 5,795,976). Although techniques such as HPLC under partially denaturing conditions are powerful for identifying poymorphisms and detecting polymorphisms in the presence of a reference nucleic acid (i.e., by the formation of a homo- or heteroduplex with the reference nucleic acid), single nucleotide changes in an allele could not be directly determined using these techniques, even under optimum conditions. (See e.g., C. G. Huber et al., Anal. Biochem. 212 (1993) 351–358).

All of the methods in use today capable of screening broadly for genetic polymorphisms suffer from technical complications and are labor and time intensive. There is a need for new methods that can provide cost effective and expeditious means for screening genetic material.

SUMMARY OF THE INVENTION

The present invention provides a method for detecting polymorphisms in a nucleic acid, e.g., DNA or RNA, by 1) preconditioning a sample of nucleic acids to completely denature the nucleic acids, e.g., via heating and/or chemical treatment; and 2) performing high-performance liquid chromatography (HPLC) on the sample under denaturing conditions to identify the polymorphism of the nucleic acid. The nucleic acids to be analyzed are completely denatured prior to application of the sample to a stationary reverse-phase support and throughout the HPLC process. The sample mixture is eluted with a mobile phase containing an ion-pairing reagent and an organic solvent. Sample elution is also carried out under completely denaturing conditions.

The nucleic acid sample to be analyzed is generally injected and pre-mixed with the mobile phase prior to elution on the solid support. The sample is preferably injected into a pre-conditioned mobile phase, though it can also be passed through a "preconditioning" tubing or pre-column placed between injector and column. This allows the sample to equilibrate before contact with the solid support, and provides a means for denaturation of the sample, e.g., by heating of the mobile phase-sample mixture or by contact of the sample with the alkaline environment of the mobile phase.

The stationary phase used in the present methods may be any reverse phase solid support, including monolith stationary phases and stationary phases based on particles. Reverse phase columns or column packing materials for use in the invention are typically composed of alkylated polymeric solid support materials such as silica, cellulose and cellulose derivatives such as carboxymethylcellulose, alumina, zirconia, polystyrene, polyacrylamide, polymethylmethacrylate, and styrene copolymers. In a preferred embodiment, the polymeric base material is a styrene-divinyl copolymer. Typically, the stationary support is composed of beads from about 1–100 microns in size.

The mobile phase contains an ion-pairing agent and an organic solvent. Ion-pairing agents for use in the method include lower primary, secondary and tertiary amines, lower trialkylammonium salts such as triethylammonium acetate and lower quaternary ammonium salts. A preferred tertiary amine is triethyl amine. Typically, the ion-pairing reagent is present at a concentration between about 0.05 and 1.0 molar. Organic solvents for use in the method include solvents such as methanol, ethanol, 2-propanol, acetonitrile, and ethyl acetate.

In one embodiment, the method of the invention utilizes thermal means to provide and maintain completely denaturing conditions of the mobile phase and the stationary phase during HPLC. When denaturation of the sample is provided by heating, preferably the apparatus used in performing the HPLC, e.g., the sample loop, preconditioning coil, and the column, are all maintained at a sufficient temperature to maintain denaturation of the nucleic acid in the sample.

In another embodiment of the invention, completely denaturing conditions are achieved and maintained by the presence of a compound that increases the pH of the mobile phase, e.g. NaOH. Sample elution is then carried out under pH conditions effective to maintain complete denaturation of the nucleic acids. In such cases, a lower column temperature (less than about 65° C.) may be sufficient for determining polymorphisms in the sample.

In one particularly preferred embodiment of the present method, analysis of the nucleotide sequence of an oligomer is determined by applying a sample containing an oligomer to a C-18 alkylated polystyrene-divinylbenzene copolymer stationary support and eluting the mixture with a mobile phase containing triethylammonium acetate as the ion-pairing reagent and acetonitrile as the organic solvent at a temperature between about 70°–80° C.

An advantage of the present invention is that the majority of possible transitions and transversions can be typed accurately.

Another advantage of the invention is that the method of the present invention can be used in conjunction with other methods of detecting and analyzing polymorphisms, e.g., detection by means of HPLC based heteroduplex detection under partially denaturing conditions and analysis using methods such as mass spectrometry.

The invention also provides a method for direct discrimination of alleles using completely denaturing HPLC. A DNA oligomer (e.g., an amplicon produced from a genetic region containing a known SNP) is amplified from the individual to be analyzed and the selected polymorphic site contained therein is identified using the separation method of the present invention. The polymorphism is detected by the sequence of the oligomer, and thus does not require the use of a reference oligomer to determine the presence of the polymorphism.

Isolation may be accomplished through any number of methods, including but not limited to amplification (e.g., PCR) or reverse transcription, and restriction digestion and purification. HPLC is performed using a reverse phase column. Such methods provide a fast, efficient and inexpensive method of direct allelic discrimination which does not require a positive control to identify single base polymorphisms.

It is an object of the present invention to provide methods for allelic discrimination using direct detection of nucleotide differences by HPLC analysis of PCR-generated amplicons.

It is an advantage of the present method that the oligomers may be rapidly genotyped without the need of a reference chromosome.

It is an advantage of the present method that the oligomers to be analyzed may be isolated using any number of different methods, including reverse transcription and PCR.

The invention also provides methods to diagnose and/or determine prognosis and appropriate treatment methods for a subject using the methods of the invention. The present methods of identifying polymorphisms can be used to identity nucleotide changes associated with a disease state, with a predisposition for a disease, with a particular prognosis, or with response to a particular therapeutic treatment.

It is yet another object of the present invention to detect polymorphisms to be used as genetic markers and/or diagnostic tools. This includes polymorphisms in regions of either high or low mutation, including polymorphisms in regions known to have great genetic variability across a population, mutations that are causative of a disorder. The present methods can also be used to detect very rare somatic mutations.

In another embodiment, a selected set of one or more single nucleotide polymorphisms is determined for a given group or population, and the information stored in a data storage computer system, e.g., a relational database system.

The invention also provides the production of polymorphism databases produced using the present methods. Such databases may be produced for any number of purposes such as forensic identification of an individual, linkage analysis, population studies, epidemiological surveys, and the like.

These and other objects, advantages, and features of the invention will become apparent to those persons skilled in the art upon reading the details of the protocols as more fully described below.

DETAILED DESCRIPTION OF PREFERRED EMBODIMENTS

Figure 1:
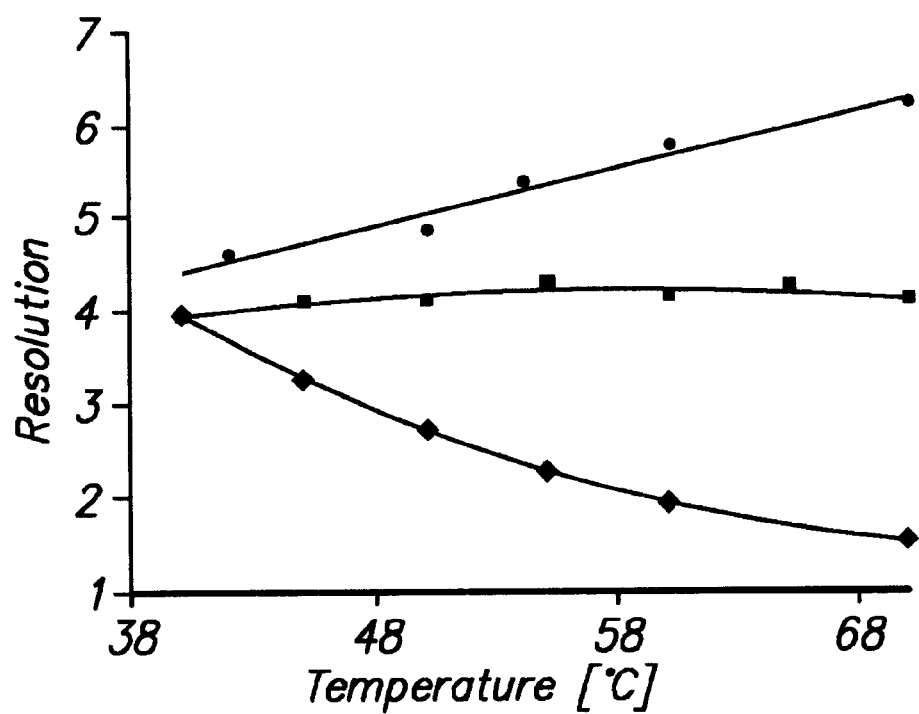
FIG. 1 is a line graph illustrating the impact of heating and instrument configuration on the resolution of oligodeoxythymidylic acids: (♦) sample loop and 80-cm preconditioning coil outside the oven, (●) only 80-cm preconditioning coil in the oven, and (■) both sample loop and 80-cm preconditioning loop placed inside the oven.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an amplicon" includes a plurality of such amplicons and reference to an "SNP" includes reference to one or more SNPs in a nucleic acid and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "reverse phase" and "reverse phase support" as used herein refer to any stationary support, including the base material and any chemically bonded phase, for use in high performance liquid chromatography (HPLC) which is less polar (e.g., more hydrophobic) than the starting mobile phase. The term is intended to encompass a porous and/or a non-porous a support "Alkylated", "alkylation" and the like as used herein in reference to the solid support refers to attachment of hydrocarbon chains to the surface of particles of the solid support, typically ranging about 3 to 22 carbon atoms in length. The hydrocarbon chains may be saturated or unsaturated and may optionally contain additional functional groups attached thereto. The hydrocarbon chains may be branched or straight chain and may contain cyclic groups such as cyclopropyl, cyclopropyl-methyl, cyclobutyl, cyclopentyl, cyclopentylethyl, and cyclohexyl. Typically, an alkylated solid support refers to an extent of alkylation of the base material of greater than about 50 percent.

"Lower alkyl" refers to an alkyl radical of one to six carbon atoms, as exemplified by methyl, ethyl, n-butyl, i-butyl, t-butyl, isoamyl, n-pentyl, and isopentyl.

"Organic solvent" as used herein, refers to a component of the mobile phase utilized in reverse phase ion pairing HPLC. The organic solvent, occasionally referred to as an organic modifier, is any organic (e.g., non-aqueous) liquid suitable for use in the chromatographic separation methods of the present invention. Generally, the organic solvent is a polar solvent (e.g., more polar than the stationary support) such as acetonitrile or methanol.

"Ion-pair (IP) chromatography" as used herein refers to any chromatographic method for separating samples in which some or all of the sample components contain functional groups which are ionized or are ionizable. Ion-pair chromatography is typically carried out with a reverse phase column in the presence of an ion-pairing reagent.

"Ion-pairing reagent" is a reagent which interacts with ionized or ionizable groups in a sample to improve resolution in a chromatographic separation. As used herein, ion-pairing agent refers to both the reagent and aqueous solutions thereof. An ion-pairing agent is typically added to the mobile phase in reverse phase HPLC for optimal separation. The concentration and hydrophobicity of an ion-pairing agent of choice will depend upon the number and types (e.g., cationic or anionic) of charged sites in the sample to be separated.

The term "polymorphism" as used herein refers to any detectable polymorpohism in DNA or RNA that is detectable using the present methods. The term as used herein encompasses, for example, polymorphisms associated with a disease state (i.e. mutations), "silent" polymorphisms (i.e. associated with a wild-type phenotype or in a non-coding region), and polymorphisms associated with a predisposition and/or response to treatment (i.e. a polymorphism in an allele of a gene, e.g., apoE). Polymorphisms can be small deletions, insertions, single nucleotide changes, and the like.

The terms "single nucleotide polymorphism" and "SNP" refer to polymorphisms of a single base change.

The term "genetic region" as used herein refers to a specific region on a chromosome which may be isolated for detection of a polymorphism.

The term "oligomer" as used herein refers to any nucleic acid, including DNA and RNA, having a plurality of nucleotides. In the present methods, oligomers for determining nucleotides by HPLC are preferably less than 1000 nucleotides long, more preferably less than 500 nucleotides long, and even more preferably are less than 100 nucleotides long.

The term "amplicon" as used herein refers to an oligomer prepared using PCR amplification of a selected genetic region in an individual.

The phrase "completely denaturing conditions" as used herein refer to the conditions under which nucleic acids are analyzed in the present invention. The term as used encompasses complete to substantially complete denaturation conditions, i.e. a sufficient number of nucleic acids are denatured to allow resolution using HPLC protocols. Preferably, completely denaturing conditions will provide denaturation of at least 90%, more preferably at least 95%, and even more preferably at least 99.5% of the nucleic acid molecules in the sample.

General Aspects of the Invention

The present invention is based on the scientific observation that high-performance liquid chromatography can be used to resolve single nucleotide changes in single-stranded nucleic acids by subjecting the nucleic acids to reverse phase HPLC under completely denaturing conditions. The methods of the invention provide successful resolution of heterooligonucleotides differing only in a single base, irrespective of the location of the substitution. The method of the present invention requires only small amounts (typically less than about 100 nanograms) of sample, yields results in minutes, utilizes on-line detection, and is adaptable to complete automation. In addition, the reagents used in the present techniques are less costly than reagents required for other techniques such as fluorescent detection of polymorphic markers.

The methods of the present invention improve resolution of oligonucleotides significantly, by maintaining continuous, complete denaturation of the nucleic acids at temperatures higher than 65° C. throughout the process, e.g., by heating both the sample loop and the mobile phase of the column to a temperature sufficient to provide denaturing conditions. For example, both the sample loop and an 80-cm coil of polyether ether ketone (PEEK) tubing, through which the mobile phase is run prior to injection, may be placed in the column oven. Positioning only the coil in the oven, but not the injection loop, resulted in neither an improvement nor a decrease in resolution of the oligonucleotides. See FIG. 1. Resolution of the nucleic acid sequences improved increasingly with increasing length of the tubing placed between the injector and the column. The same effect can be obtained by placing the coil in front of the injector with the sample loop being mounted inside the oven.

The observed improvement in the resolution of oligonucleotides is also reflected in a significant increase in the number of theoretical plates. The number of theoretical plates increased from $4.58 \times 10^5$ to $8.50 \times 10^5$ and $3.75 \times 10^5$ to $6.33 \times 10^5$ plates/m, respectively, for a phosphorylated and dephosphorylated hexadecamer of oligodeoxy-thymidylic acid upon increase of the column oven temperature from 40 to 80° C.

Figure 2:
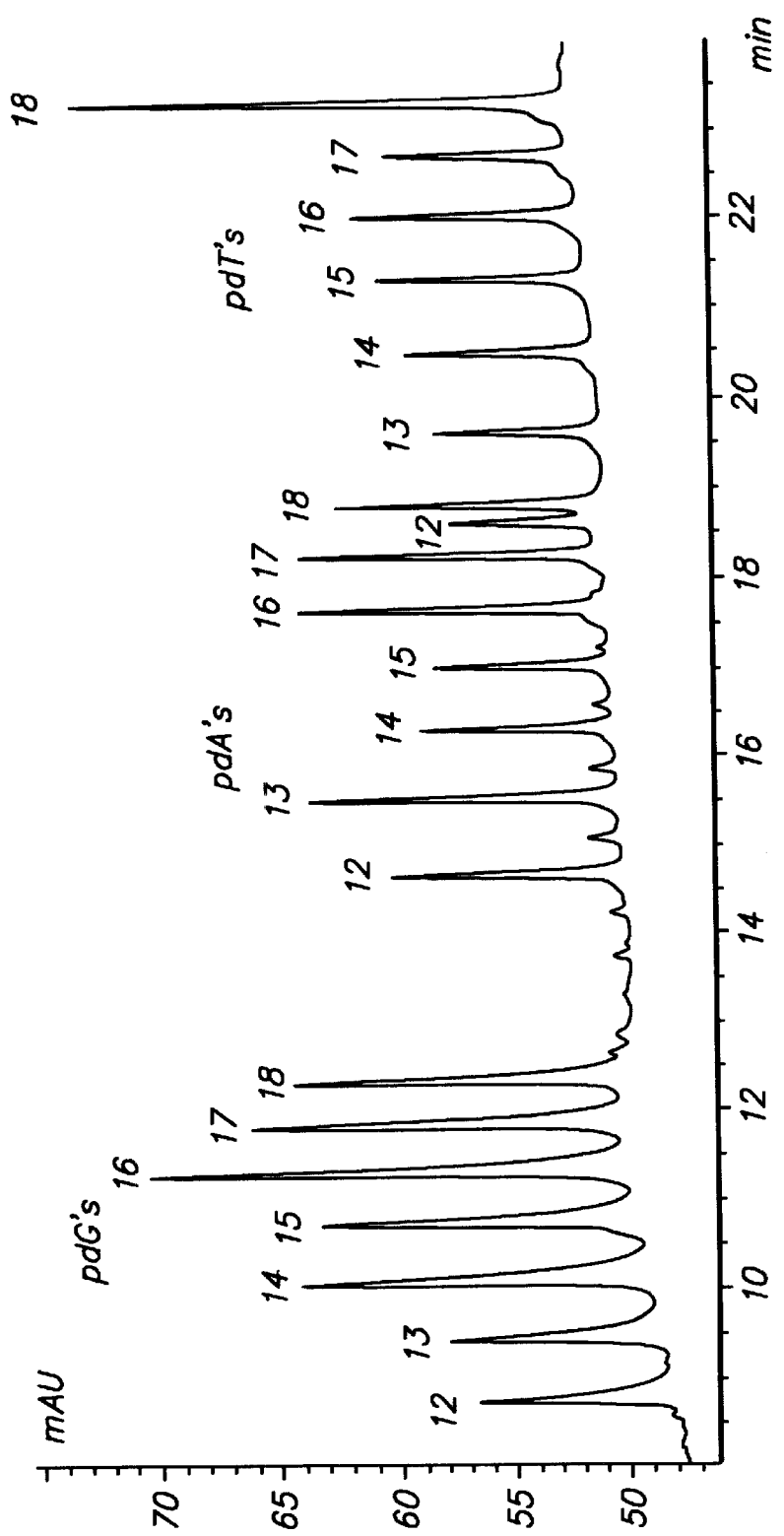
FIG. 2 is a graph illustrating separation of phosphorylated homo-oligonucleotides under thermally denaturing conditions.

Using the completely denaturing conditions, it is possible to resolve oligomers (e.g., oligodeoxy-guanylic acids) that could not separated previously by means of ion-pair reversed-phase HPLC. FIG. 2 shows the simultaneous separation of homooligonucleotides in the size range of 12–18 bases. In agreement with a previous study of homotetramers (C. G. Huber et al., LC-GC 14 (1996) 114–127), the homooligomers eluted in the order G<C<A<T. The originally observed elution order is corroborated by the present study for a set of four 16-mer heterooligonucleotides differing again in a single base at the 3'-end. Without being bound to any specific theory, it can be speculated that retention of isomeric oligo-nucleotides that exhibit roughly the same degree of electrostatic interaction with the ion-pairing reagent is controlled by differences in the hydrophobicity of the bases located at the 3'-end and by their hydrophobic interaction with the stationary phase.

HPLC under completely denaturing conditions can be used for direct allelic discrimination without prior addition of a known homozygous reference as is required for high-performance liquid chromatography under partially denaturing conditions (P. A. Underhill, et al., Genome Res. 7 (1997) 996–1005; A. Hayward-Lester et al., in: F. Ferré (Ed.), *Gene Quantification*, Birkhäuser Verlag, 1997, pp. 44–77). A recent study evaluating the use of high-density oligonucleotide arrays for the purpose of genotyping biallelic markers observed that only approximately 60% of a total of 487 biallelic markers proved amenable to allelic discrimination by this approach (R. J. Cho et al., Nature Genet. 23 (1999) 203–207.). Therefore, the demonstrated ability of HPLC to discriminate nucleotide level changes constitutes a significant improvement over other conventional methods in the art. The ability of the ion-pair reversed-phase HPLC protocols of the present invention to resolve at elevated column temperatures the single-stranded components of short PCR products, e.g., even when they differ only in a single base expands the utility of high-performance liquid chromatography in genetic studies. Importantly, it also complements the proven ability of partially denaturing HPLC to detect single-base mismatches in amplicons as long as 1 kb and constitutes an inexpensive and readily automated approach to the scoring of biallelic markers in disease association studies and gene mapping by means of linkage disequilibrium.

Preconditioning of Nucleic Acid in a Sample

The sample to be analyzed is preconditioned prior to application to the stationary phase to effect complete denaturation of the nucleic acid molecules within the sample. Denaturation of the nucleic acids may be provided using methods known to those skilled in the art, as will be apparent to one skilled in the art upon reading the present disclosure, and all such methods compatible with the technique of reverse phase HPLC are intended to be encompassed by the present application. Two exemplary techniques for effecting denaturation of nucleic acids, thermal denaturation and alkaline denaturation, are described herein in more detail.

Thermal Denaturation

Preconditioning of the sample using thermal denaturation generally requires mixture of the sample with an adequately preheated and/or chemically treated mobile phase that results in the instantaneous complete denaturation of the nucleic acid in the sample. The temperature of the sample is preferably at least 65° C. The mobile phase components can be introduced into a mixer inside the column oven and mixed prior to contact with the sample. Preferably, the sample is injected into the mobile phase and pre-equilibrated to the temperature of the column, i.e., a temperature sufficient to provide complete denaturation of the nucleic acids in the sample. This allows for a fairly direct connection between the column and the injector to minimize diffusion and enhance sample resolution.

Where a low-pressure HPLC system is used, sample mixing typically occurs at ambient temperature. In instances in which the autosampler does not provide for heating, the HPLC tubing (e.g., 0.005–0.01" diameter) may be positioned between the injector and the column, to heat the mobile phase and induce denaturation of the nucleic acid ion the sample. The tubing is preferably fitted with hardware such as that made of PEEK or titanium. The length of the tubing is typically determined based upon the efficiency of heat transfer. Preferably, the entire length of the pre-column is maintained at oven temperature. The sample is passed through the pre-column and then contacted with the stationary phase for subsequent elution. Detection was achieved using an 80 cm length of heated tubing between the injector and the column, with the total length maintained at a column temperature of 70° C. Longer tubing may also be used to enhance the denaturation by providing a longer expanse over which the sample is heated.

The pH of the mobile phase used in thermal denaturation can vary depending upon the concentrations of various components. For separation of nucleic acid samples such as RNA or DNA oligomers, using temperature to denature the nucleic acid, the pH of the mobile phase is typically maintained between about 7 and 9. For example, the mobile phase is maintained at a pH around 7.5. Alternatively, the pH may be increased to ensure the denaturation of the nucleic acid in the sample.

The optimal column temperature will in part depend upon the sequence (base composition) of the sample to be separated, the choice of stationary phase, the choice of mobile phase, pH, flow rate, and the like, and in many cases, will be determined empirically. Ideally, in cases with known sequence, a suitable column temperature may be calculated that will provide denaturation of at least 90%, more preferably at least 95%, and even more preferably at least 99.5% of the nucleic acid.molecules in the sample.

The composition of the sample sequence to be analyzed also affects the parameters to be selected for carrying out the separation method of the invention. For samples containing a polymorphic site flanked by a GC-rich region, higher temperatures may be required to detect the polymorphism.

Thermal denaturation obviates the need to add denaturing chemicals such as formamide to the sample (M. B. Arghavani et al., 231 (1995) 201–209) or to work under highly alkaline pH conditions as shown for the separation of oligonucleotides on a strong anion-exchanger (W. A. Ausserer and M. L. Biros, BioTechniques 19 (1995) 136–139). In addition, the use of thermal denaturation does not result in added chemicals to the mobile phase, which is especially useful if the eluted sample is to be subjected to additional analysis, e.g., mass spectrometry, since chemical components used for denaturation or produced during denaturation (e.g., salt precipitates) may interfere with the procedure of the subsequent analysis or be detrimental to equipment.

Denaturation via Alkaline Environment

Alternatively or in conjunction with thermal denaturation, the nucleic acid in the sample may be denatured by adjusting the pH of the sample and/or mobile phase prior to application to the column. The pH may be adjusted by the addition of a base (e.g., sodium hydroxide or urea to a pH of greater than about 9) under conditions effective to completely denature nucleic acid molecules. Conditions are chosen that do not degrade the nucleic acids present in the sample nor adversely affect the integrity of the stationary phase. When chemical preconditioning of the sample is used, sample elution may be carried out at lower temperatures, e.g., at or less than about 50° C., and preferably from about 50° C. to about 65° C. Alternatively, the altered pH of the mobile phase may be used in conjunction with heat to ensure complete denaturation of the product.

Denaturing High Performance Liquid Chromatography

High performance liquid chromatography (HPLC) generally refers to a technique for partitioning a sample or more specifically the components of a sample between a liquid moving or mobile phase and a solid stationary phase. In the present invention, the applicants have discovered a chromatographic method which utilizes completely denaturing conditions to enable the identification of single nucleotide differences in a short nucleic acid irrespective of the position of the nucleotide difference.

Stationary Phase

In the method of the present invention, a sample containing denatured nucleic acid molecules are applied to a stationary phase. Generally, the stationary phase is a reverse phase material in which the chemically bonded phase is hydrophobic and is less polar than the starting mobile phase. Any of a number of commercially available reverse phase solid supports may be utilized in the present nucleic acid separation method, although the resolution may vary depending upon the nature of the sample and other relevant experimental parameters, as will be apparent to one skilled in the art upon reading the present disclosure. Reverse phase columns or column packing materials for use in the invention are typically composed of alkylated polymeric base materials such as silica (Eriksson, et al.), cellulose and cellulose derivatives such as carboxymethylcellulose, alumina, zirconia, polystyrene, polyacrylamide, polymethylmethacrylate, and styrene copolymers. In a preferred embodiment, the polymeric base material is a styrene-divinyl copolymer. Typically, the stationary support is composed of beads from about 1–100 microns in size.

The base materials composing the solid support are typically alkylated. Alkylation of the base material prevents secondary interactions and can improve the loading of the stationary phase with the ion-pairing reagent to promote conversion of the solid support into a dynamic anion-exchanger. Typically, the solid support is alkylated to possess alkyl groups containing at least 3 carbon atoms, generally between about 3 and 22 carbon atoms, and preferably contains between about 4 and 18 carbon atoms. The base material is alkylated to contain at least 50% surface alkyl groups, and preferably, at least 90% of the surface base material is covered. The alkylated solid support phase may optionally contain functional groups for surface modification. The presence or absence of such functional groups will be dictated by the nature of the sample to be separated and other relevant operational parameters.

Various types of alkylating reagents may be used to alkylate the polymeric solid support. Alkylation may take place either after formation of the polymeric beads as described in Example 1 or before (e.g., by utilizing alkylated monomers to produce alkylated co-polymer beads). Alkylation may be carried out by any of a number of synthetic approaches depending upon the base support material to be alkylated. In an exemplary method for alkylating polymeric base materials containing aryl groups such as polystyrene-divinylbenzene, alkylation is carried out using the Friedel-Crafts reaction, utilizing either tin tetrachloride or aluminum chloride as the Lewis acid catalyst. Alternatively, one may utilize commercially available reverse phase supports containing surface alkyl groups, such as those available from Hamilton (Reno, Nev.) or Hewlett Packard (Wilmington, Del.).

A stationary phase for use in the present method may be either porous or non-porous. A porous stationary phase may contain more than one type of pore or pore system, e.g, containing micropores (less than about 50 Å) and/or macropores (greater than about 1000 Å). The stationary phase will typically have a surface area of about 2–400 m$^2$/g, and preferably about 8–20 m$^2$/g as determined by nitrogen adsorption.

The separation method of the present invention utilizes denaturing HPLC, and more specifically, ion-pairing reverse phase HPLC (IP-RP-HPLC). In carrying out the separation according to the present method, the aqueous mobile phase contains an ion-pairing agent and an organic solvent. The selection of aqueous mobile phase components will vary depending upon the nature of the sample and the degree of separation desired. Any of a number of mobile phase components typically utilized in ion-pairing reverse phase HPLC are suitable for use in the present invention. Several mobile phase parameters (e.g., pH, organic solvent, ion-pairing reagent and counterion, elution gradient) may be varied to achieve optimal separation, as will be apparent to one skilled in the art based on the present disclosure.

Ion-pairing reagents for use in the invention are those which interact with ionized or ionizable groups in a sample to improve resolution including both cationic and anionic ion-pairing reagents. Cationic ion-pairing agents for use in the invention include lower alkyl primary, secondary and tertiary amines, such as triethylamine (TEA), lower trialkylammonium salts of organic or inorganic acids such as triethylammonium acetate, and lower quaternary ammonium salts such as tetrabutylammonium phosphate. Anionic ion-pairing agents include perfluorinated carboxylic acids.

The hydrophobicity of the ion-pairing agent will vary depending upon the nature of the desired separation. For example, tetrabutylanimonium phosphate is considered a strongly hydrophobic cation while triethylamine is a weak hydrophobic cationic ion-pairing reagent. Generally, preferred ion-pairing agents are cationic in nature. One such preferred ion-pairing agent for use in the invention is triethylammonium acetate (TEAA).

The concentration of the ion-pairing agent in the mobile phase is typically between about 0.05 and 1.0 molar, with a preferred concentration of about 0.1 molar. Generally, sample resolution is improved with increasing concentrations of ion-pairing agent. Trialkylammonium salts appear to be useful for obtaining good size-based separation for AT-rich sequences.

Organic solvents for use in the mobile phase are generally polar solvents such as acetonitrile, methanol, ethanol, ethyl acetate, and 2-propanol. A preferred solvent is acetonitrile.

The concentration of the mobile phase components will vary depending upon the nature of the separation to be carried out. The mobile phase composition may vary from sample and during the course of the sample elution. Gradient systems containing two or more components may be used.

Samples are typically eluted by starting with an aqueous or mostly aqueous mobile phase containing an ion-pairing agent and progressing to a mobile phase containing increasing amounts of an organic solvent. Any of a number of gradient profiles and system components may be used to achieve the denaturing conditions of the present invention. One such exemplary gradient system in accordance with the invention is a linear binary gradient system composed of (i) 0.1 molar triethylammonium acetate and (ii) 25% acetonitrile in a solution of 0.1 molar triethylammonium acetate Allelic Discrimination using Denaturing HPLC The present methods are especially useful in discriminating between two or more alleles having distinct polymorphisms without the need for a reference allele. This is especially useful in the case where a number of different alleles exist for a particular locus, as the present invention can distinguish the particular allele based on the actual sequence of the polymorphism or polymorphisms.

Isolation of Nucleic Acid Oligomers

The nucleic acid oligomers to be evaluated using the methods of the invention may be isolated using any number of various techniques available to one skilled in the art. For example, where it is desirable to detect a polymorphism (e.g., an SNP) in a specific genetic region, a DNA sample from an individual may be used as a template for amplification of the genetic region using the polymerase chain reaction (PCR). This methods will produce an amplicon that can be tested for the presence of a selected polymorphism. In another example, a sample may be obtained from amplification of a selected region of mRNA, e.g., a region of mRNA that may contain a mutation associated with a disease state. Suitable templates for a PCR reaction to prepare such an amplicon include, but are not limited to, DNA isolated from a subject, RNA isolated from a subject, either total or mRNA, or a cDNA library prepared from cells or tissue of a subject. The reactions themselves can be optimized by those skilled in the art based on variables such as the length of the oligomer to be amplified, the G-C content of the oligomer to be amplified, the template used, and the like. See e.g., PCR Strategies, eds. by M. A. Innis, D. H. Gelfand , J. J. Sninsky and J. I. Sninksy both of which are incorporated herein by reference.

In another example, a nucleic acid region of interest can also be isolated using a technique such as reverse transcription of RNA. The RNA used as template for the reverse transcriptase may be preselected (e.g., through oligo-dT selection) or total RNA. Enzymes that may be used in the reverse transcriptase reaction include, but are not limited to, commercially available enzymes such as Avian Myeloblastosis Virus (AMV) Reverse Transcriptase and MoMLV Reverse Transcriptase.

In yet another example, a nucleic acid region of interest may be isolated using a combination and/or modification of reverse transcription and PCR techniques, such as reverse-transcribed PCR (RT-PCR). These and other methods are described in detail in *The PCR Technique: RT-PCR* (The BioTechniques Update Series)—ed. P. D. Siebert (1998), which is incorporated herein by reference.

In yet another example, a nucleic acid region of interest may be isolated by restriction endonuclease digest and purification of a selected oligomer containing a polymorphism, e.g., an SNP. The DNA is optionally enriched prior to the restriction digest (e.g., purification of a particular region of a chromosome using a technique such as pulse-filed gel electrophoresis). DNA is digested and purified using techniques known in the art (Sambrook et al., Molecular Cloning: A Laboratory Manual Cold Spring Harbor Laboratory Press, Vol. 2 (1989).

The nucleic acid oligomers to be analyzed using the methods of the invention are preferably shorter oligomers, e.g., oligonucleotides ranging from 2 to 200 nucleotides in length, and more preferably oligomers from about 40–90. Thus, although the methods of the invention described herein are described with respect to and optimized for shorter oligonucleotides, the methods can be optimized to distinguish single base polymorphisms in longer oligomers as will be apparent to one skilled in the art upon reading the present specification.

The method of the present invention may be enhanced by other factors that affect resolution of the nucleic acids using HPLC. For example, the use of nucleotide analogs, such as deoxyinosine or 7-deazaguanine, in the isolation of oligomers may be used to aid in the elucidation of particular polymorphisms Production of Databases Using Methods of the Present Invention The methods of the present invention may be used to generate a database having data on selected polymorphisms of individuals, such as subjects affected with a disorder or individuals convicted of particular crimes. Such databases may be produced using a variety of different data configurations and processing capabilities. Examples include, but are not limited to, logical databases, physical databases, relational databases, central configuration databases, and the like. For example, the data generated using the present methods may be used to create a general database such as that described in U.S. Pat. No. 4,970,672 or a relational database such as that described in U.S. Pat. No. 5,884,311. Databases containing data generated using the methods of the invention may also be a central configuration database for data that is shared among multiprocessor computer systems. See U.S. Pat. No. 6,014,669. Other database systems and design methodologies can be found in I. Fogg and M. Orlowska, *Computers Math. Applic.* (UK), (1993) 25:97–106; S. Ceri, et al., Proceedings of the IEEE (1987) 75:533–545.

Utility of the Present Invention

The methods of the invention have utility in a wide variety of fields where it is desirable to identify known polymorphisms of a particular individual and/or to determine allelic distribution in a group or population. Such methods include, but are not limited to, linkage analysis for the identification of disease loci, evolutionary studies to determine rates of evolution in a population, identification of polymorphisms useful in forensic identification, identification of mutations associated with a disease or predisposition, genetic marker development, and the like.

The present method facilitates the identification of the frequency of known genetic markers that are both physically and genetically mapped. SNPs can be determined for an individual, without using a comparative control sample, to identify the individual, e.g. to forensically identify an individual based on DNA evidence at a crime scene. Specific polymorphic sites may be quantified in a selected group (e.g., individuals in families with a history of a genetic disorder) or population (e.g., individuals of a certain race or ethnicity) to determine the presence of an SNP in that group or population.

Using the present denaturing HPLC method, large numbers of DNA samples can be rapidly and efficiently screened for the presence or absence of polymorphisms, and only those samples identified in the pre-screening as possessing polymorphic sites need be further characterized, typically by conventional sequencing techniques. Such genomic analysis can be performed using any genomic nucleic acid material, for example, from mammals, birds, fish, reptiles, plants, microorganisms, or other organisms of interest.

The present method can also be used for forensic applications such as DNA fingerprinting. DNA fingerprinting requires the identification of a set of polymorphic loci, selected so that the probability that two individual DNA samples with identical haplotypes could by chance come from different individuals is very low. The method provides an efficient approach for identifying low mutating polymorphic sites along lengths of contiguous sequence such that the probability of recombination is quite low, increasing the likelihood of the preservation of haplotype information desirable for forensic utilization.

In addition to analysis of genome diversity, the method of the present invention can be applied to the analysis of any number of microorganisms including bacteria, parasites, and other infectious agents. This may be especially useful in the determination of a particular strain of an infectious organism, e.g., the strain of Human Immunodeficiency Virus (HIV) or bacteria from an infected individual. Determination of the particular infectious microorganism can aid in prognosis of the disease as well as in the treatment of the individual, e.g. a particular strain can determine the aggressiveness of treatment of an infected individual as well as providing a rational basis for the selection of a therapeutic regime.

The method of the present invention can also be applied to the analysis of any nucleic acid containing entity, including subcellular organelles such as chloroplasts and mitochondria. Such methods may be useful for determining disorders associated with mitochondrial mutations (e.g., omithine trans-carbamylase deficiency) or for evolutionary studies involving mutation rates in organelles, such as mapping of mitochondrial DNA.

Further, the method of the present invention can also be used in screening methods for the evaluation of predispositions for disorders and the use and/or efficacy of therapeutic treatments for the treatment or prevention of such disorders, e.g. Alzheimer's disease, Huntington's disease, cancer predisopsitions such as Li-Fraumeni syndrome, and the like. For example, a specific allele of the apolipoprotein gene, apoE4, is associated with an increased risk for development of Alzheimer's disease (M. Kanai et al., Neurosci Lett. (1999) 267:65–8; Mirra SS. *Hum Pathol.* (1999) 30:1125–7). The present method provides an efficient and inexpensive method for determining the presence or absence of this allele in an individual, and thus can be predictive of the disease in an individual. Moreover, certain therapeutic agents may be particularly effective for an individual having a particular allele, such as the apoE4 allele, and so identification of the allele also identifies an individual who is a good candidate for treatment with a particular therapy.

Additionally, phylogenetic relationships can be established by the method of the present invention. Phylogenetic analysis can be carried out with almost any selected genomic sequence, such as, glycolytic enzymes (like phosphoglycerate kinase (Vohra, et al.)) or rRNA sequences. Phylogenetic relationships between plants can be established, using, for example, sequences derived from plastid ribosomal RNA operons (Wolfe, et al.).

Use of the Present Method in Concert with Other Techniques

The methods of the present invention can also be used in concert with other protocols for detecting, isolating and/or analyzing polymorphisms or other attributes of nucleic acids. Exemplary protocols for use with the present invention include isolation of heteroduplex molecules using HPLC and analysis of nucleic acid fragments using mass spectrometry, both of which are described briefly below.

Use of the Invention in Concert with Heteroduplex Identification by HPLC

The present methods complement other protocols to allow low cost analysis of biallelic markers in hundreds of samples. For example, the present methods can be used in conjunction with the detection of SNPs by DHPLC (see U.S. Pat. No. 5,795,976) to isolate and analyze a large number of new SNPs in a fast, efficient and inexpensive manner. This methods involves separating heteroduplex and homoduplex nucleic acid molecules (e.g., DNA or RNA) in a mixture using high performance liquid chromatography under partially denaturing conditions. This method provides a fast and effective method for identifying new polymorphisms, including SNPs. Once these polymorphisms are identified, the methods of the present invention can be used to detect the newly identified polymorphism in large numbers of samples.

Use of the Invention in concert with Mass Spectrometry

Mass spectrometry can be used in conjunction with the methods of the present invention to verify a polymorphism and/or to identify additional polymorphisms. The mass spectrum of an oligomer can be obtained is compared to the mass spectrum of fragments obtained from known samples of either wild-type genes or genes containing the known mutation. These known spectra are referred to as "signature" spectra. A simple comparison of the sample spectrum vs. signature spectra will reveal whether the patient's DNA contains a mutation. Although sequencing of fragments of nucleic acids is possible using mass spectrometry, actual sequencing of the nucleic acid is not required for this mutational analysis. Less preparation and analysis is needed to prepare and analyze a complete, intact fragment as compared to treating a sample for actual sequencing.

Certain mass spectrometry techniques can be used to analyze for polymorphisms. Short oligomers, e.g., from one nucleotide up to approximately 50 nucleotides, can be analyzed and the resulting spectra compared with signature spectra of samples known to be wild-type or to contain a known polymorphism. A comparison of the locations (mass) and heights (relative amounts) of peaks in the sample with the known signature spectra indicate what type of polymorphism, if any, is present. Exemplary protocols are described in U.S. Pat. Nos. 5,872,003, 5,869,242, 5,851,765 5,622,824, and 5,605,798, which are incorporated herein by reference for teaching such techniques.

Use of the Present Method to Produce a Database for SNPs

A need remains for a general catalog of genome variation to address the large-scale sampling designs required by association studies, gene mapping, and evolutionary biology. There is widespread interest in documenting the amount and geographic distribution of genetic variation in the human species. This information is desired by the biomedical community, who want a densely packed map of SNP (single nucleotide polymorphism) sites to be used to identify genes associated with disease by linkage disequilibrium between sets of adjacent markers and the occurrence of disease in populations, and to characterize disease-related variation among populations.

Anthropologists and archeologists use genetic variation to reconstruct our species' history, and to understand the role of culture and geography in the global distribution of human variation. The requirements for these two perspectives seem to be converging on a need for an accessible, representative DNA bank and statistical database of human variation.

In addition, these systems have potential in both routine forensic and intelligence database applications, either in place of or in conjunction with more traditional "DNA fingerprinting" databases produced using methods such as restriction fragment length polymorphism mapping.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Initial Detection of SNPs Using Thermal Denaturation

Initial experiments to evaluate the effect of temperature on the separation of oligonucleotides were performed using HPLC on a chromatograph consisting of an on-line vacuum degassing system (Alltech, Deerfield, Ill.), an automatic sampling system equipped with a biocompatible injection valve and a 20-µL Titanium sample loop (Model AS-100 T HRLC®, Bio-Rad, Hercules, Calif.), a high precision low pressure gradient pump (Model 480, Gynkotek, Germering, Germany), a column oven (Model CH-150, Eldex), a UV-VIS detector (Model Spectra 100, Thermo Separation Products, Riviera Beach, Fla.), a multichannel interface (Dual Channel Interface HP 35900E, Hewlett Packard, Mountain View, Calif.), and a PC-based data system (G1304A, Version A.02.05, Hewlett Packard). For the pre-heating of the mobile phase, an 80-cm PEEK tubing, 0.01-inch I.D., which had been encased in a tin-alloy block (Part No. 330-HX, Timberline, Inc., Boulder, Colo.), was used.

The column and conditions used for identifying SNPs was as follows: DNASep™, 50×4.6 mm I.D.; mobile phase: 0.1 M TEAA, pH 7.0; linear gradient: 3.75–6.25% acetonitrile in 15 min; flow-rate: 1 ml/min; temperature: 50 to 80° C.; detection: UV, 254 nm; sample: 16 and 22 mer oligonucleotides, 0.15 µg each. Peak identification was determined for the nuclewotides underlined below as follows:

TABLE 1

Sequences Used For Initial Detection of SNPs Under Thermally Denaturing Conditions

| c, TCCATGAATCACTCCC; | (SEQ ID NO:1) |
| g, TCCATGAATCACTCCG; | (SEQ ID NO:2) |

TABLE 1-continued

Sequences Used For Initial Detection of SNPs Under Thermally Denaturing Conditions

| a, TCCATGAATCACTCCA; | (SEQ ID NO:3) |
| t, TCCATGAATCACTCCT; | (SEQ ID NO:4) |
| G, GTGCTCAGTGTGGCCCAGGATC; | (SEQ ID NO:5) |
| C, GTGCTCAGTGTCGCCCAGGATC; | (SEQ ID NO:6) |
| A, GTGCTCAGTGTAGCCCAGGATC; | (SEQ ID NO:7) |
| T, GTGCTCAGTGTTGCCCAGGATC; | (SEQ ID NO:8) |

Figure 3:
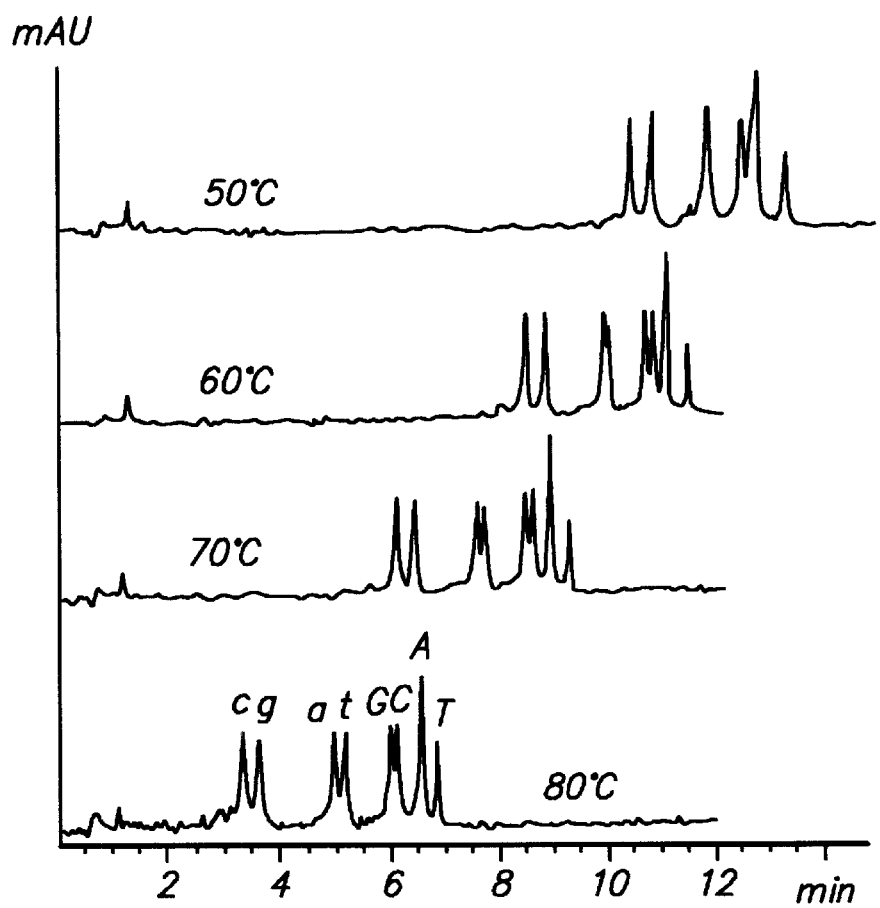
FIG. 3 is a graph illustrating the impact of temperature on the separation efficiency of 16- and 22-mer heterooligonucleotides that differ in a single base at either the 3'-end or in the center of the molecule.

Notably, resolution of the latter two oligonucleotides (SEQ ID NOS: 7 and 8) improves significantly with an increase in column temperature from 50 to 80° C., while that of the former two (SEQ ID NOS: 5 and 6) decreases slightly. More importantly, an increase in column temperature allowed the almost complete baseline resolution of four isomeric heterooligonucleotides identical in sequence except for a single base substitution at the 12th nucleotide from the 5'-end (FIG. 3). At present, it remains unclear why the elution order of the latter set of heterooligonucleotides (SEQ ID NOS: 5 through 8) corresponded to that of homooligonucleotides (see FIG. 2), while substitution of the base at the 3'-end results in a reversal of the elution order of cytosine and guanine.

Example 2

Determination of Effect of Thermal Denaturation on HPLC Resolution

In order to determine the impact of heating on the resolution of oligonucleotides using HPLC, a number of different oligonucleotides having varying sequences were analyzed. The sequences investigated are listed as follows in Table 2.

TABLE 2

List of sequences amplified to genotype the single-nucleotide polymorphisms given in brackets. Priming sites are written in Lower case.

| SNP No. | 5'—3' | Amplicon size |
|---|---|---|
| SNP1 | aaaccacattctgagcataccccc[C/A]AAAAATTtcatgccgaagctgtggtc<br>(SEQ ID NOS:9 AND 10) | 51bp |
| SNP2 | caacttaatcagatttaggacacaaaagc[A/T]actacataatgaaaagagagctggtga<br>(SEQ ID NOS:11 AND 12) | 58bp |
| SNP3 | gaaacggcctaagatggttgaaT[C/C]ctctttattttctttaatttagacatgttcaaa<br>(SEQ ID NOS:13 AND 14) | 58bp |
| SNP4 | gactttttgtacccaccatttgtCcAACTAAATT[A/C]Tatcagtacaaaaagggctacattc<br>(SEQ ID NOS:15 AND 16) | 60bp |
| SNP5 | agacagttcttcaggaaaacaccT[C/T]CTTTGGAcTCAcAccatgtgttttccattcaaatta<br>(SEQ ID NOS:17 AND 18) | 61bp |
| SNP6 | cccaaacccatttgatgctT[G/T]ACTTAAaaggtcttcaattattattttcttaaatattttg<br>(SEQ ID NOS:19 AND 20) | 62bp |
| SNP7 | ccattgaggaacaacatacagcTTCTCTTCC[C/A]cctcggctgtgggctc<br>(SEQ ID NO:21 AND 22) | 48bp |
| SNPB | aataaacctttacggggctaagcCT[C/T]agacctgcaagctgcttgttatag<br>(SEQ ID NO:23 AND 24) | 50bp |
| SNP9 | agacatctgactcccagcatgaa[C/T]GGTCccaactcctctctaacaaaaggtaa<br>(SEQ ID NO:25 AND 26) | 53bp |
| SNP10 | tttgttcatacggtcaatattcgat[A/T]CTCTCAGtcctcactgctggtccttacg<br>(SEQ ID NOS:27 AND 28) | 54bp |
| SNP11 | cgaaaaagaagatggtgagttcacTTTT[T/C]acctcaataaaaccctttacataaa<br>(SEQ ID NOS:29 AND 30) | 54bp |
| SNP12 | gctccatttgaaggttctataactgAAACTAGAATAC[C/A]TAAgctatggggaactaaa<br>ctctgaat<br>(SEQ ID NOS:31 AND 32) | 65bp |
| SNP13 | gataagccatatgatccagcaggATTAATTCCTTTTAC[C/T]GTTTAATTAgtcgtagat<br>actcaagacagaccgt<br>(SEQ ID NOS:33 AND 34) | 73bp |

TABLE 2-continued

List of sequences amplified to genotype the single-nucleotide polymorphisms given in brackets. Priming sites are written in Lower case.

| SNP No. | 5'—3' | Amplicon size |
|---|---|---|
| SNP14 | tgtcctttagtttctatttggttttATATATTATCATATGAACTATAAAGAAG[G/A]Tt gaagcaaagaacagccaaataat (SEQ ID NOS:35 AND 36) | 79bp |
| SNP15 | tggagtatttctctagcttgctgAAATAATG[C/G]CAAATTTTATAATATGATACTAGCAA CACAAATATTTAgctaaaattacgttgcattaaaaa (SEQ ID NOS: 37 AND 38) | 94bp |

The position and chemical nature of the SNP are given in brackets and the priming sites are written in lower case. All oligonucleotide primers were obtained from Life Technologies (Rockville, Md., USA). Phosphorylated and dephosphorylated oligodeoxyadenylic acids, oligodeoxycytidylic acids, oligodeoxyguanylic acids and oligodeoxythymidylic acids, 12–18 bases in length, were purchased from Amersham Pharmacia Biotech, Inc. (Piscataway, N.J., USA). All PCR reagents and 2M triethylamine acetate buffer were obtained from PE Biosystems, Foster City, Cailf., USA. HPLC grade acetonitrile was purchased from J. T. Baker (Phillipsburg, N.J., USA), tetrasodium ethylenediaminetetraacetic acid from Sigma (St. Louis, Mo., USA).

Polymerase chain reactions for isolation of each of the oligonucleotides were performed in a 50 μl volume containing 10 mM Tris-HCl, pH 8.3, 50 mM KCl, 2.5 mM MgCl$_2$, 50 μM dNTPs, 0.2 μM of each primer, 50 ng of genomic human DNA, and 1 unit of AmpliTaq Gold. The PCR cycling regime carried out in a Perkin-Elmer 9600 thermal cycler comprised an initial denaturation step at 95° C. for 10 min to activate AmpliTaq Gold. Subsequent denaturing steps were 94° C. for 20 s and extension steps of 72° C. for 60 s; annealing temperatures were lowered over the first 14 cycles in 0.5° C. decrements from 63–56° C., followed by 20 cycles at 56° C. for 45 s each. Following a final extension step at 72° C. for 10 min, samples were chilled to 6° C. and stored in a refrigerator until HPLC analysis.

Each oligonucleotide pair was anaylzed using denaturing HPLC. The stationary phase consisted of 2-μm nonporous alkylated poly(styrene-divinylbenzene) particles packed into 50×4.6-mm ID columns, which are commercially available (DNASep™, Transgenomic, San Jose, Calif., USA). The mobile phase was 0.1 M triethylammonium acetate buffer (TEAA) at pH 7.0, containing in addition 0.1 mM Na$_4$EDTA. Crude PCR products were eluted with a linear acetonitrile gradient at a flow-rate of 0.8–1.0 ml/min. The start- and end-points of the gradient were adjusted according to the size of the single-stranded DNA sequences.

Figure 4:
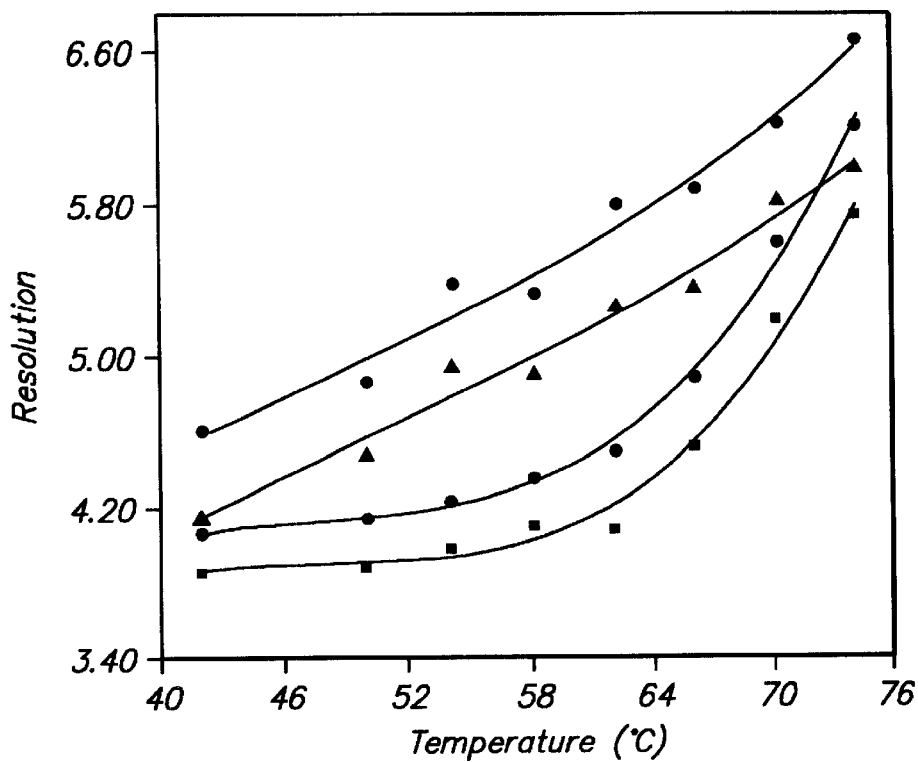
FIG. 4 is a graph showing the effect of temperature on the resolution of dephosphorylated oligodeoxyadenylic acids and phosphorylated oligodeoxythymidylic acids. The samples are as follows: ■, $d(A)_{15/16}$; ♦, $d(A)_{14/15}$; ▲$pd(T)_{15/16}$; and ●, $d(T)_{14/15}$.

Intra- and intermolecular interactions were also observed in the case of oligodeoxyadenylic acids, although they have been reported to be significantly less than those of guanine-rich sequences (F. Aboul-ela et al., Nucl. Acids Res. 13 (1985) 4811–4824). This explains why in contrast to oligothymidylic acids, which have not been observed to interact with each other, no linear increase in resolution is observed with increasing temperature for oligodeoxyadenylic acids (FIG. 4). Only at temperatures above 70° C. a resolution similar to that of oligodeoxythymidylic is obtained. This applies to both phosphorylated and dephosphorylated oligonucleotides.

Figure 5:
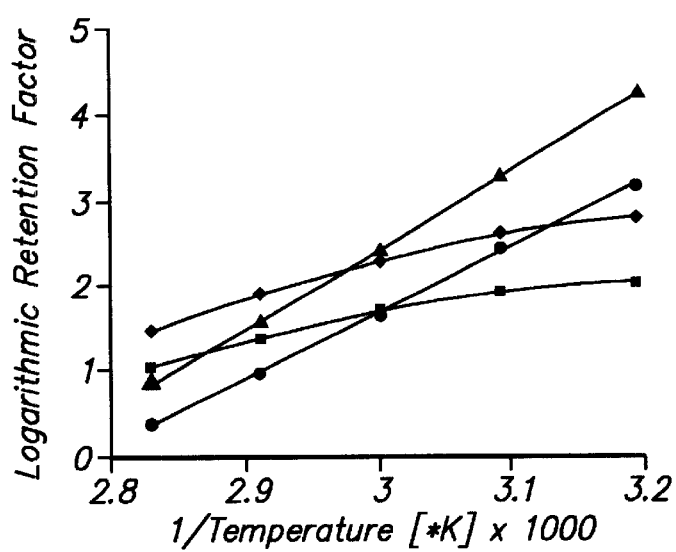
FIG. 5 is a series of Van't Hoff plots illustrating the dependence of the logarithmic retention factors of homooligonucleotides. The samples are as follows: ●, $pd(T)_{16}$; ▲, $d(T)_{16}$; ■, $pd(A)_{16}$; and ♦, $d(A)_{16}$.
Figure 6:
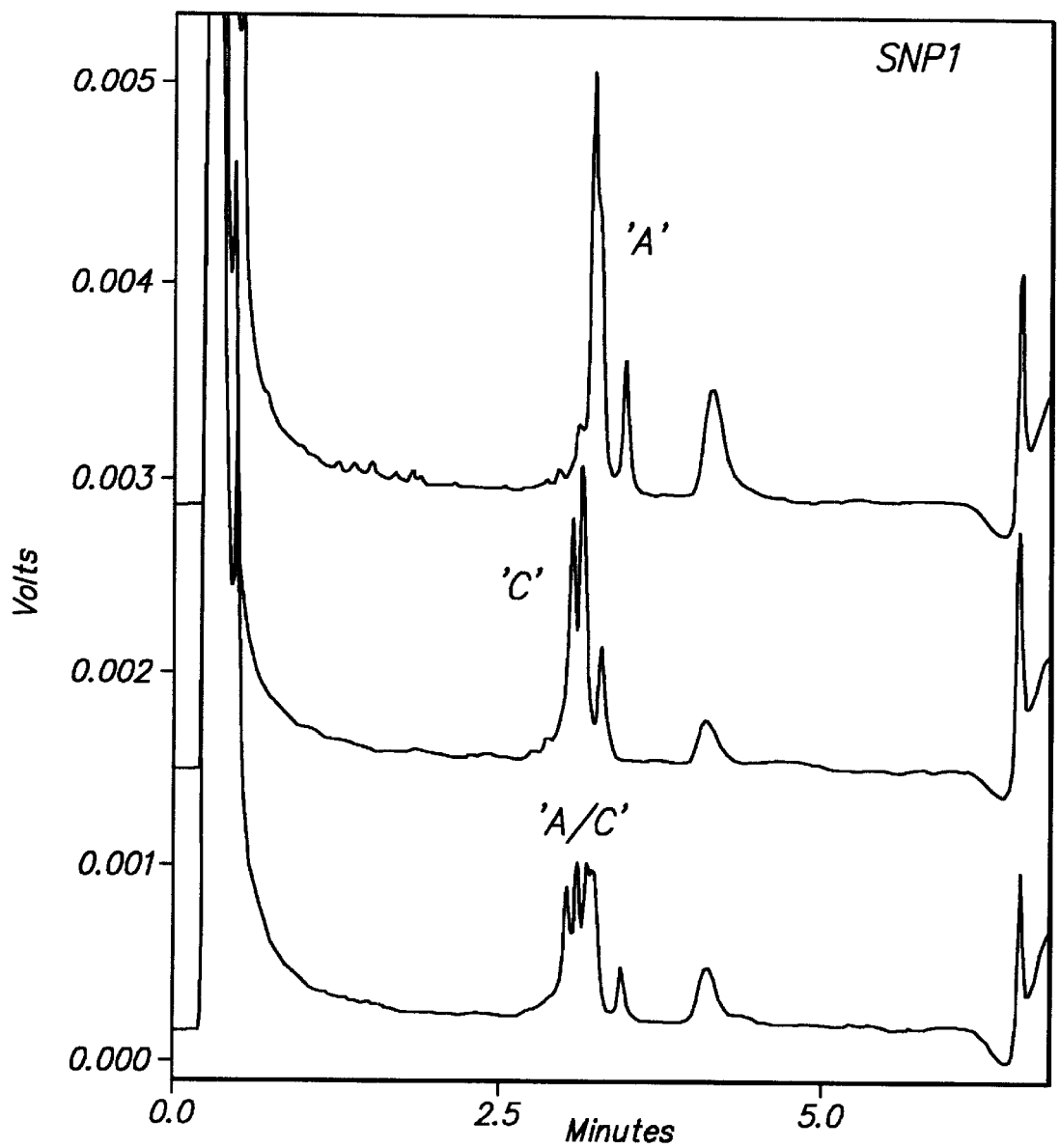
FIGS. 6–11 are a series of graphs illustrating the allelic discrimination of transitions and transversions by high-performance liquid chromatography under completely denaturing conditions.
Figure 7:
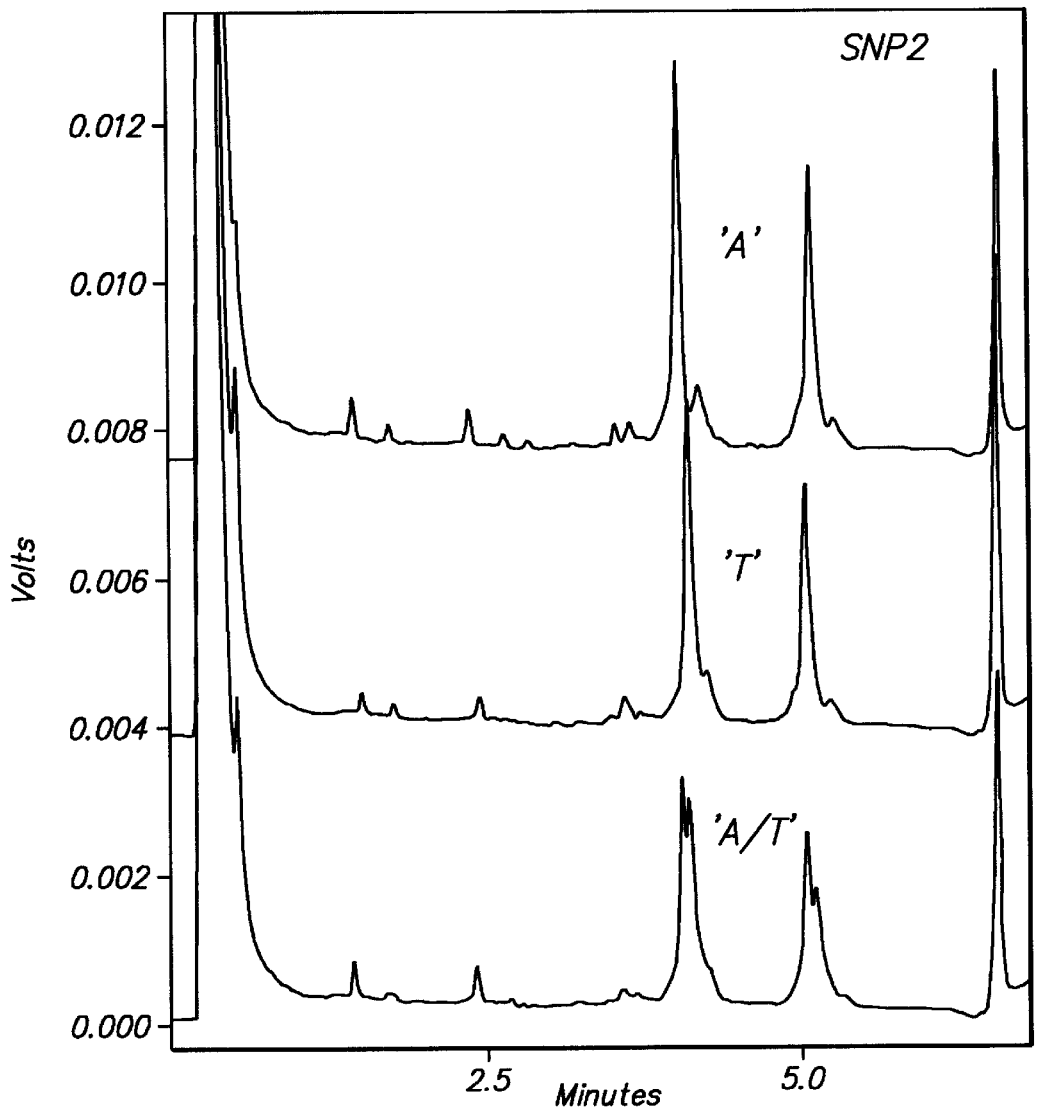
Figure 8:
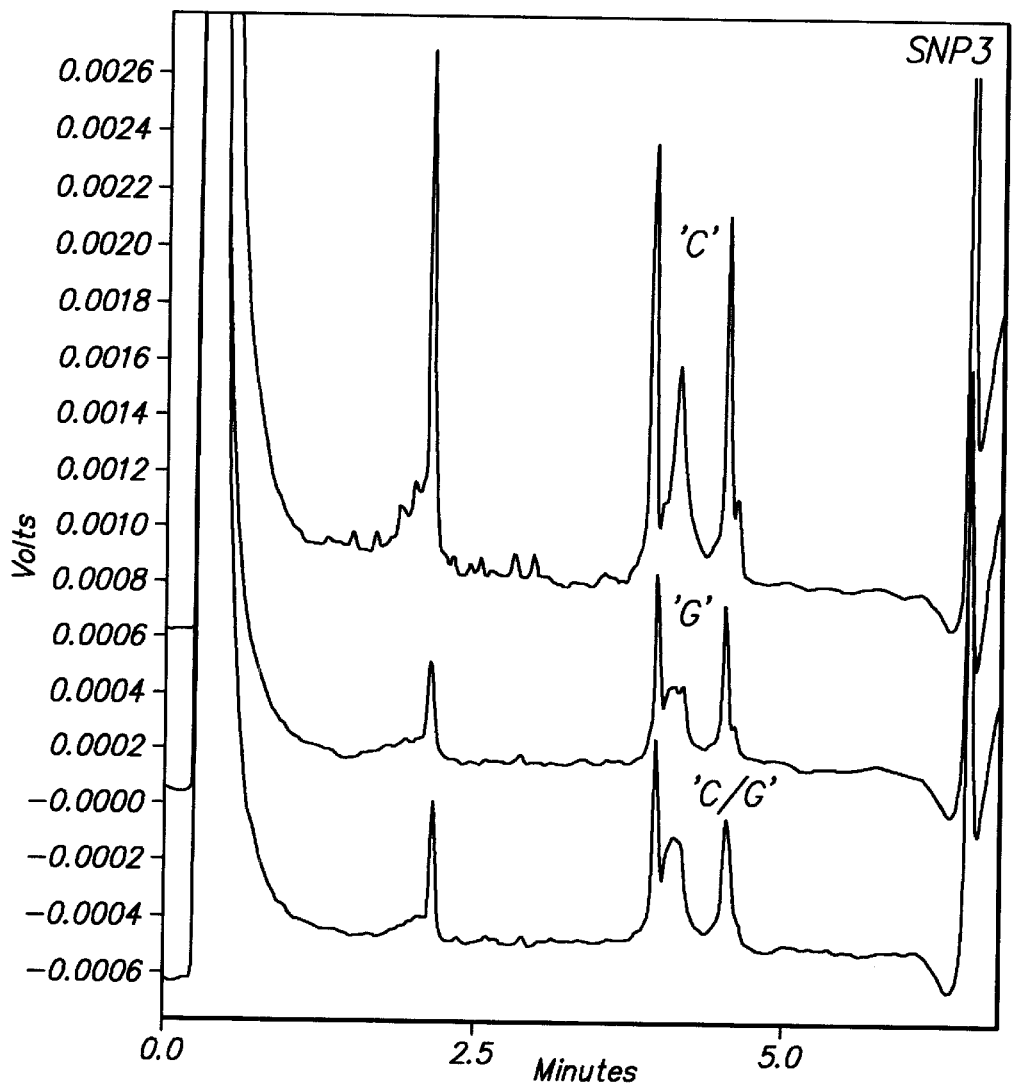
Figure 9:
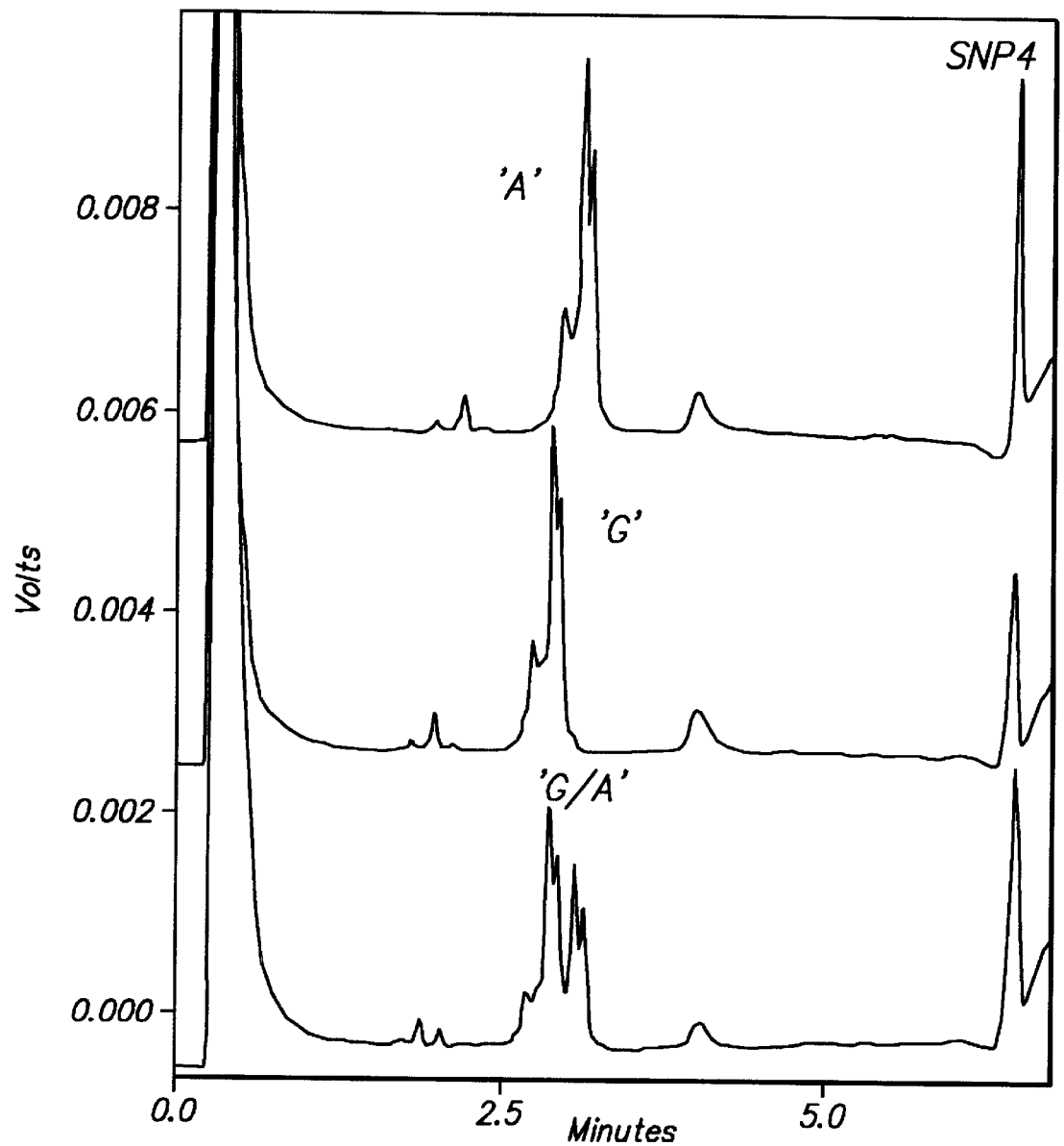
Figure 10:
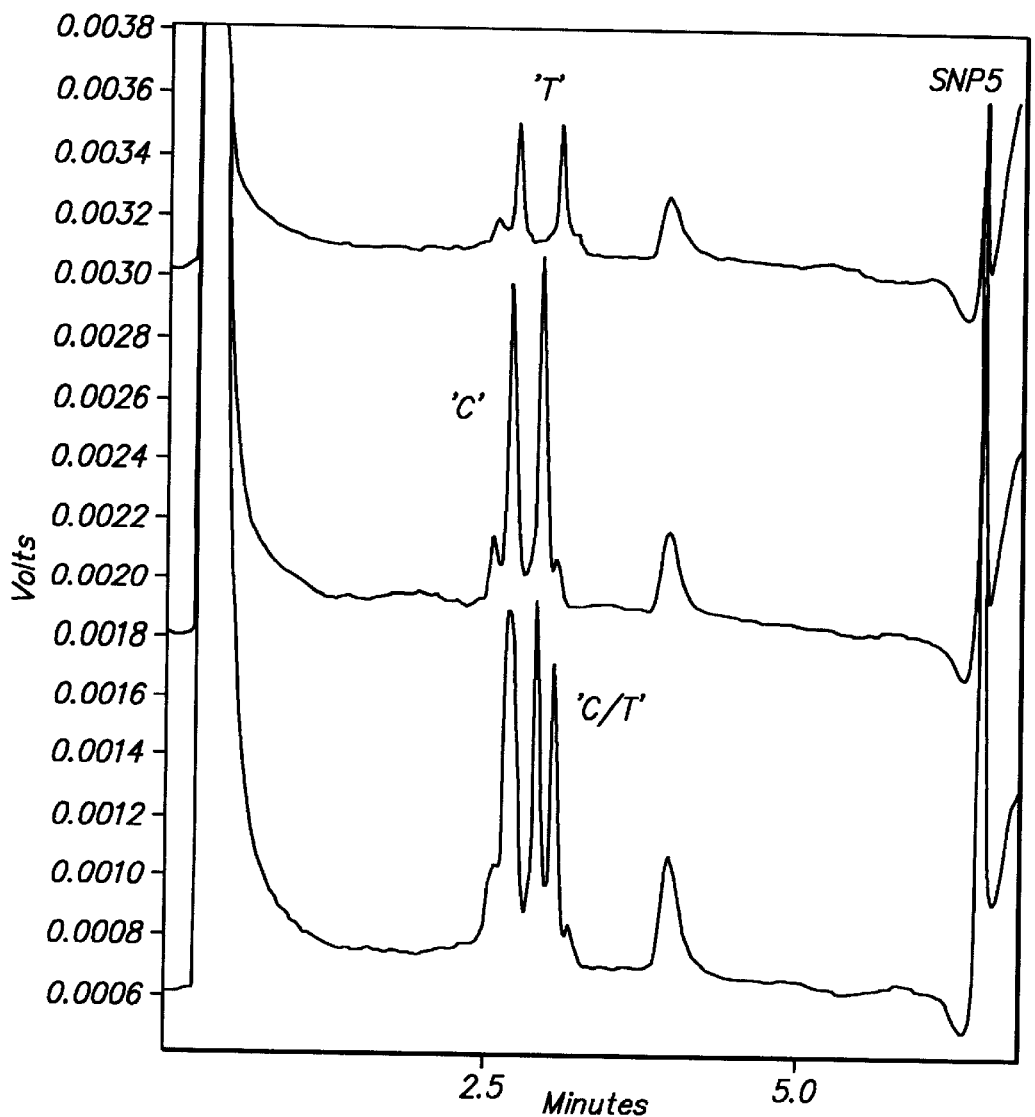
Figure 11:
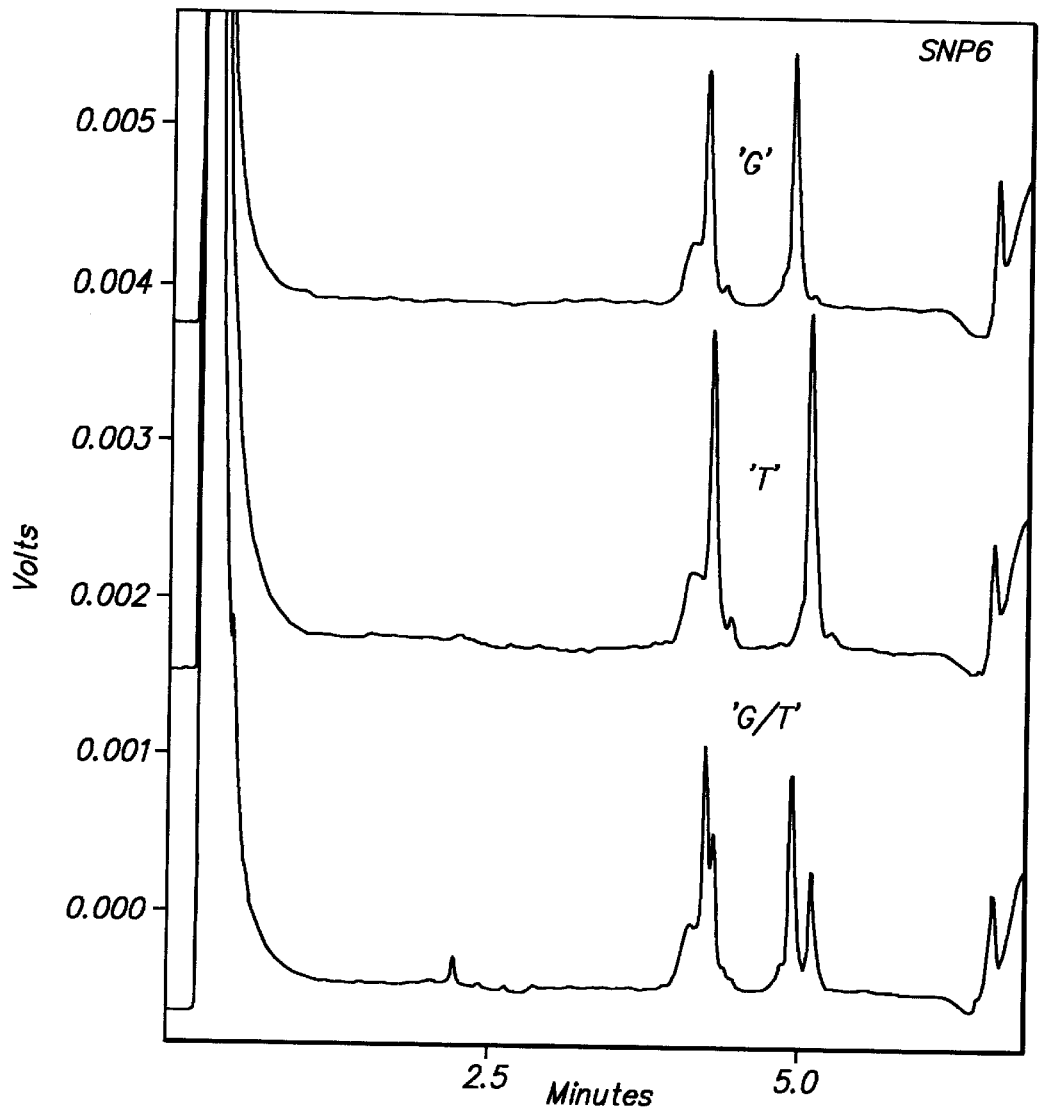

Intra- and intermolecular interactions also explain the non-linear reaction isochores observed in Van't Hoff plots for oligodeoxyadenylic acids (FIG. 5) (Due to intra- and intermolecular interactions oligodeoxyadenylic acids do not yield linear reaction isochores. The respective adsorption enthalpies for d(T)$_{16}$ and pd(T)$_{16}$ in 7.25 acetonitrile were −81.44 kJ mol$^{-1}$ and −59.36 kJ mol$^{-1}$). In contrast, linear isochores were obtained for phosphorylated and dephosphorylated oligodeoxythymidylic acids the geometry of which does not allow the formation of atypical Watson-Crick base pairs (F. Aboul-ela et al., Nucl. Acids Res. 13 (1985) 4811–4824). The plots clearly demonstrate the dependence of the logarithmic retention factors of d(T)$_{16}$ and pd(T)$_{16}$ on the reciprocal absolute temperature. In a mobile phase of 100 mM TEAA, pH 7, and 7.25% acetonitrile the adsorption enthalpies of the two oligodeoxythymidylic acids were determined to be −81.44 kJ mol$^{-1}$ and −59.36 kJ mol$^{-1}$, respectively. Similar adsorption enthalpies were determined for the two phosphorylated 18-mer heterooligonucleotides 5'TGTAAAACGACGGCCAGT (SEQ ID NO:39) and 5'CAGGAAACAGCTATGACC (SEQ ID NO:40), that were also found to yield linear reaction isochores. The respective values in 100 mM TEAA and 5.25% acetonitrile were −65.23 kJ mol$^{-1}$ and −63.80 kJ mol$^{-1}$. This indicates that phosporylation at the 5'-base has the greatest effect on the enthalpies due to the hindered hydrophobic interaction between the former and the column matrix. The difference in adsorption enthalpies between d(T)$_{16}$ and pd(T)$_{16}$ amounts to >25%.

Example III
Allelic Discrimination by Denaturing HPLC

In order to evaluate the feasibility of using denaturing HPLC for genotyping short amplicons, the primers of which flank the polymorphic site of interest and the bases in its immediate vicinity, a number of amplicons 51–62 bp in size (SNP 1–6) were generated (FIGS. 6–11). They contained biallelic sites of different chemical nature, specifically the two transitions C→T and A→G, as well as the four transversions C→A, C→G, T→A, and T→G. The protocols used for PCR and HPLC analysis were the same as for Example II, except that the temperatures used for denaturation were 75° C. for SNP1, 70° C. for SNP2, and 80° C. for SNP3–6.

The void peak comprises unincorporated nucleotides and excess primers. The peak eluting at approximately 4 minutes is a system peak. It is apparent that all but the C→G transversion could be discriminated successfully. Particularly striking is the case of the T→A transversion, which cannot be discriminated by assays such as T$_m$-shift genotyping (D. Y. Wu et al., Proc. Natl. Acad. Sci. USA 86 (1989) 2757–2760) because the substitution only results in the replacement of a T→A in one chromosome to A→T in the other chromosome. This surprising observation may be attributed to the fact that retention in HPLC is governed not only by the substituted base but also by the immediate sequence context. Further, as expected, the complementary strands of an amplicon are usually resolved well, resulting in the observation of usually two peaks in case of a homozygous sample, and four peaks in case of a heterozygous sample.

As evident from FIGS. 6–11, temperature can be used to optimize resolution. For instance, two isomeric single-stranded DNA molecules that differ in a single adenine or thymine are resolved somewhat better at a lower temperature, e.g., 70° C. (SNP2). Other mismatches are discriminated more clearly at 80° C. Generally, even an amplicon very rich in GC base pairs will be denatured completely at 70° C. due to the presence of acetonitrile in the mobile phase. Only the C→G transversions investigated, namely SNP3, were not as successfully genotyped, although partial resolution was observed at a concentration of 50 mM triethylammonium acetate in the mobile phase. Use of a different ion-pairing reagent and other modifications to the protocol may be used to provide the successful allelic discrimination of C→G transversions by HPLC.

In order to assess the reproducibility of elution profiles, we repeated the genotyping of SNP2 and SNP6 14 and 17 times, respectively. The coefficients of variation for the absolute retention times of the four major product peaks ranged from 0.4–0.6% for SNP2 and 0.3–0.4% for SNP6, respectively. An even more reliable measure is the ratio of the retention times of the two complementary strands.

In case of SNP2, the ratios for allele A and allele T were 0.794±0.003 (mean±SD, CV=0.39%) and 0.814±0.003 (CV=0.41%), respectively, with the values ranging from 0.787–0.797 and 0.806–8.818, respectively. Comparing the two means of the ratios of retention times using a t-test, they were found to differ significantly from each other ($t_s$= 17.638, $t_{0.0001[26]}$=3.707). The same was true for SNP6: the arithmetic means and standard deviations for the T allele and G allele were 0.845±0.002 (0.842–0.850, CV=0.27%) and 0.857±0.002 (0.853–0.860, CV=0.22%), respectively. Again, the t-test was highly significant ($t_s$=17.493, $t_{0.001[32]}$ ≈3.6). The high reproducibility of retention times also corroborates the excellent chemical and physical stability of poly(styrene-divinylbenzene) particles at high temperature with more than 600 analyses having been performed over a period of 10 days without any noticeable deterioration in separation efficiency.

Ultimately, it would be advantageous to couple HPLC to mass spectrometry to confirm the identity of the peaks. Past problems with the use of triethylammonium acetate that was found to reduce drastically ion formation during electrospray ionization have been overcome recently by replacing it with triethylammonium bicarbonate without affecting the proven separation efficiency of ion-pair reversed-phase HPLC. Further, in combination with acetonitrile added as a sheath liquid to the column effluent, analyte detectability in the femtomol range has been accomplished for even large oligonucleotides (C. G. Huber and A. Krajete, Anal. Chem. 71 (1999) 3730–3739).

In addition to the 6 SNPs depicted in FIGS. 6–11, we tested nine SNPs (SNP 7–15) for which genotyping information had been obtained recently by dye terminator sequencing. The HPLC based genotyping results were found to be in complete accordance with those determined by sequencing (except SNP15 that could not be genotyped at all because of the nature of the substitution).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for analyzing the nucleotide sequence of a nucleic acid in a sample, said method comprising:
   preconditioning a sample comprising a first homoduplexed nucleic acid molecule and a second homoduplexed nucleic acid molecule, wherein said first and second homoduplexed nucleic acid molecules differ by at least one base pair, said preconditioning providing a completely denatured sample comprising single-stranded nucleic acid molecules, and wherein said preconditioning is by the addition of a compound that increases the pH of the sample;
   applying the completely denatured sample to a stationary reverse phase support while maintaining complete denaturation of the nucleic acid; and
   eluting the completely denatured sample under completely denaturing conditions using a mobile phase comprising an ion-pairing reagent and a solvent;
   wherein said eluting results in the resolution of the single-stranded nucleic acid molecules such that single-stranded nucleic acid molecules that differ in sequence by one nucleotide are separately resolved.

2. The method of claim 1, where said eluting is carried out at a temperature between about 50° C. and 65° C.

3. The method of claim 1, where the stationary support is an alkylated support.

4. The method of claim 1, wherein the support comprises a material selected from the group consisting of silica, alumina, zirconia, polystyrene, polyacrylamide, and styrene-divinyl copolymers.

5. The method of claim 3, where the surface of said support is alkylated with hydrocarbon chains containing from 4–18 carbon atoms.

6. The method of claim 1, further comprising the steps of:
   isolating said first and second homoduplexed nucleic acid molecules; and
   preparing said first and second homoduplexed nucleic acid molecules in a sample for analysis of the nucleotide sequence.

7. The method of claim 6, wherein said first and second homoduplexed nucleic acid molecules are isolated using a technique selected from the group consisting of polymerase chain reaction, reverse transcription, reverse-transcribed polymerase chain reaction, restriction endonuclease digestion, and cloning and hybridization selection.

8. The method of claim 1, where the mobile phase contains an ion-pairing agent selected from the group consisting of lower alkyl primary, secondary, and tertiary amines, lower trialkylammonium salts, lower quaternary ammonium salts, triethylamine, tetrahydrofuran, and triethylammonium acetate.

9. The method of claim 1, wherein the mobile phase is comprised of an organic solvent selected from the group consisting of methanol, ehtanol, acetonitrile, ethyl acetate, and 2-propanol.

10. A method for analyzing nucleic acid in a sample, said method comprising:
    preconditioning a sample using a preconditioning apparatus, the sample comprising a first homoduplexed nucleic acid and a second homoduplexed nucleic acid molecule, wherein said first and second homoduplexed nucleic acid molecules differ by at least one base pair, said preconditioning providing a completely denatured sample comprising single-stranded nucleic acid molecules;
    applying the completely denatured sample to a stationary reverse phase support while maintaining complete denaturation of the nucleic acid; and
    eluting the completely denatured sample under completely denaturing conditions using a mobile phase comprising an ion-pairing reagent and a solvent;
    wherein the preconditioning apparatus and the stationary reverse phase support are configured to maintain a sufficient temperature to allow continuous, complete denaturation of the nucleic acid in the sample, and wherein said eluting results in the resolution of the single-stranded nucleic acid molecules such that single-stranded nucleic acid molecules that differ in sequence by one nucleotide are separately resolved.

11. The method of claim 10, wherein a preconditioning loop, a sample loop, and the stationary reverse phase support are maintained at the same temperature.

12. The method of claim 11, wherein the preconditioning loop, the sample loop, and the stationary reverse phase support are both placed in a column oven.

13. The method of claim 10, wherein the preconditioning apparatus comprises a sample loop and a preconditioning loop, and further wherein the sample loop and the preconditioning loop are maintained at the same temperature as the stationary reverse phase support.

14. The method of claim 10, where the stationary support is an alkylated support.

15. The method of claim 10, wherein the support comprises a material selected from the group consisting of silica, alumina, zirconia, polystyrene, polyacrylamide, and styrene-divinyl copolymers.

16. The method of claim 3, where the surface of said support is alkylated with hydrocarbon chains containing from 4–18 carbon atoms.

17. A method for detecting polymorphisms in an allele, the method comprising the steps of:
    isolating first and second homoduplexed nucleic acid molecules, each molecule spanning a genetic region of said polymorphism, wherein said first and second homoduplexed nucleic acid molecules differ by at least one base pair;
    preconditioning the first and second homoduplexed nucleic acid molecules on a preconditioning apparatus to provide a completely denatured sample comprising single-stranded nucleic acid molecules wherein said preconditioning is by subjecting the first and second homoduplexed nucleic acid molecules to a temperature sufficient to completely denature the first and second homoduplexed nucleic acid molecules;
    applying the completely denatured sample to a stationary reverse phase support while maintaining complete denaturation of the nucleic acid; and
    eluting the completely denatured sample under completely denaturing conditions using a mobile phase comprising an ion-pairing reagent and a solvent;
    wherein the preconditioning apparatus and the stationary reverse phase support are configured to maintain a sufficient temperature to allow continuous, complete denaturation of the nucleic acid in the sample, and wherein said eluting results in the resolution of the single-stranded nucleic acid molecules such that single-stranded nucleic acid molecules that differ in sequence by one nucleotide are separately resolved, wherein resolution of at least four single-stranded nucleic acid molecule indicates the presence of a polymorphic allele.

18. The method of claim 17, wherein the first and second homoduplexed nucleic acid molecules are isolated from nuclear DNA, and wherein the method is used to identify a mutation associated with the presence of disease.

19. The method of claim 17, wherein the first and second homoduplexed nucleic acid molecules are isolated from a mammal, and wherein the polymorphism is associated with predisposition to a disease, prognosis of a disease state, and response of therapeutic effectiveness.

20. The method of claim 17, wherein the first and second homoduplexed molecules are isolated from a mammal, and wherein the polymorphism is associated with prognosis of a disease state.

21. The method of claim 17, wherein the first and second homoduplexed nucleic acid molecules are isolated from a mammal, and wherein the polymorphism is associated with response of therapeutic effectiveness.

22. A method for analyzing the nucleotide sequence of a nucleic acid in a sample, said method comprising:

preconditioning a sample comprising a first homoduplexed nucleic acid molecule and a second homoduplexed nucleic acid molecule, wherein said first and second homoduplexed nucleic acid molecules differ by at least one base pair, said preconditioning providing a completely denatured sample comprising single-stranded nucleic acid molecules, and wherein said preconditioning is by the addition of a compound that increases the pH of the sample to greater than about 9.0;

applying the completely denatured sample to a stationary reverse phase support while maintaining complete denaturation of the nucleic acid; and eluting the sample under completely denaturing conditions using a mobile phase comprising an ion-pairing reagent and a solvent;

wherein said eluting results in the resolution of the single-stranded nucleic acid molecules in the sample such that single-stranded nucleic acid molecules that differ in sequence by one nucleotide are separately resolved.

23. The method of claim 17, wherein said polymorphism is a single nucleotide polymorphism.

24. The method of claim 17, wherein said preconditioning is by heating the first and second homoduplexed nucleic acid to a temperature above about 65° C.

25. The method of claim 17, wherein said preconditioning is by heating the first and second homoduplexed nucleic acid to a temperature above about 70° C.

26. The method of claim 17, wherein said eluting is carried out at a temperature between about 70° C. and about 80° C.

27. A method for analyzing the nucleotide sequence of a nucleic acid in a sample, said method comprising:

preconditioning a sample comprising a first homoduplexed nucleic acid molecule and a second homoduplexed nucleic acid molecule, wherein said first and second homoduplexed nucleic acid molecules differ by at least one base pair, said preconditioning providing a completely denatured sample comprising single-stranded nucleic acid molecules, and wherein said preconditioning is by subjecting the sample comprising the first and second homoduplexed nucleic acid molecules to a temperature sufficient to completely denature the first and second homoduplexed nucleic acid molecules;

applying the completely denatured sample to a stationary reverse phase support while maintaining complete denaturation of the nucleic acid; and eluting the completely denatured sample under completely denaturing conditions using a mobile phase comprising an ion-pairing reagent and a solvent;

wherein the preconditioning apparatus and the stationary reverse phase support are configured to maintain a sufficient temperature to allow continuous, complete denaturation of the nucleic acid in the sample, and wherein said eluting results in the resolution of the single-stranded nucleic acid molecules such that single-stranded nucleic acid molecules that differ in sequence by one nucleotide are separately resolved.

28. The method of claim 27, wherein said preconditioning is by heating the sample comprising the first and second homoduplexed nucleic acid molecules to a temperature above about 65° C.

29. The method of claim 27, wherein said preconditioning is by heating the sample comprising the first and second homoduplexed nucleic acid molecules to a temperature above about 70° C.

30. The method of claim 27, wherein said eluting is carried out at a temperature between about 70° C. and about 80° C.

* * * * *